United States Patent
Varkey et al.

(10) Patent No.: US 9,388,473 B2
(45) Date of Patent: Jul. 12, 2016

(54) SEQUENCES AND THEIR USE FOR DETECTION OF SALMONELLA

(71) Applicant: E. I. du Pont de Nemours and Company, Wilmington, DE (US)

(72) Inventors: Stephen Varkey, Newark, DE (US); Daniel R. DeMarco, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 314 days.

(21) Appl. No.: 13/670,883

(22) Filed: Nov. 7, 2012

(65) Prior Publication Data

US 2013/0115600 A1    May 9, 2013

Related U.S. Application Data

(60) Provisional application No. 61/557,469, filed on Nov. 9, 2011.

(51) Int. Cl.
*C12P 19/34* (2006.01)
*C12Q 1/68* (2006.01)

(52) U.S. Cl.
CPC .............. *C12Q 1/689* (2013.01); *C12Q 1/6853* (2013.01)

(58) Field of Classification Search
CPC ........... C12Q 1/6853; C12Q 2525/301; C12Q 2565/1015; C12Q 1/689
USPC ....................................... 435/91.2
See application file for complete search history.

(56) References Cited

U.S. PATENT DOCUMENTS

| | | | |
|---|---|---|---|
| 4,678,812 A | 7/1987 | Bollin, Jr. et al. | |
| 4,683,195 A | 7/1987 | Mullis et al. | |
| 4,683,202 A | 7/1987 | Mullis et al. | |
| 4,762,857 A | 8/1988 | Bollin, Jr. et al. | |
| 5,210,015 A | 5/1993 | Gelfand et al. | |
| 5,487,972 A | 1/1996 | Gelfand et al. | |
| 5,538,848 A | 7/1996 | Gelfand et al. | |
| 5,804,375 A | 9/1998 | Gelfand et al. | |
| 6,312,930 B1 | 11/2001 | Tice et al. | |
| 6,326,145 B1 | 12/2001 | Whitcombe et al. | |

FOREIGN PATENT DOCUMENTS

| | | |
|---|---|---|
| EP | 0320308 | 11/1993 |
| WO | WO 94/13832 | 6/1994 |
| WO | WO 95/33854 | 12/1995 |
| WO | WO 97/11197 | 3/1997 |
| WO | WO 2004/092408 | 10/2004 |

OTHER PUBLICATIONS

Carrino et al., "Nucleic Acid Amplification Methods", J. Microbiol. Methods 23: 3-20, (1995).
Pfeffer et al., "Applications of DNA amplification techniques in veterinary diagnostics", Veterinary Res. Comm. 19: 375-407, (1995).
Tabor et al., "A Bacteriophage T7 RNA Polymerase/Promoter system for Controlled Exclusive Expression of Specific Genes", Proc. Natl. Acad. Sci. U.S.A. 82:1074-1078 (1985).
Corresponding International Search Report and Written Opinion in PCT/US2012/063799, mailed Nov. 7, 2012.
Reynisson et al., "Evaluation of probe chemistries and platforms to improve the detection of real-time PCR", J. Microbiol. Methods 66:206-216 (2006).
Office Action from corresponding Chinese Application No. 2102800549319, dated Jan. 20, 2016.
Anonymous: "Scorpion Primers", Aug. 4, 2004, XP055238143, Retrieved from the Internet: URL:https://web/archive.org/web/20040804044028/http:// www.premierbiosoft.com/tech_notes/Scorpion.html [retrieved on Dec. 22, 2015].
Office Action from corresponding European patent application No. 12787320.6-1403, date Jan. 7, 2016.

*Primary Examiner* — Cynthia B Wilder

(57) ABSTRACT

This invention relates to a rapid method for detection of *Salmonella* in a sample based on the presence of nucleic acid sequences, in particular, to a PCR-based method for detection, and to oligonucleotide molecules and reagents and kits useful therefore. In certain embodiments, the method is employed to detect *Salmonella* in a food or water sample. The present invention further relates to isolated polynucleotides, replication compositions, and kits for carrying out the method of the present invention.

8 Claims, 3 Drawing Sheets

| Primer-Probe Complex | 5' Mod-ification | 5' Stem SEQ ID | 5' Stem Sequence | Probe (Loop) SEQ ID | Probe (Loop) Sequence | 3' Stem SEQ ID | 3' Stem Sequence | Internal Modification | Primer SEQ ID | Primer Sequence |
|---|---|---|---|---|---|---|---|---|---|---|
| S35C610-1 | Cal Fluor Red 610 | 112 | AGGGACCC | 13 | TGCCGACACCAGCGCCCG | 120 | GGGTCCCT | [BHQ2][SP-18] | 47 | TAGCCGGGACGCTT AATGCGGTTAAC |
| S35C610-2 | Cal Fluor Red 610 | 113 | AGGACCC | 13 | TGCCGACACCAGCGCCCG | 122 | GGGTCCT | [BHQ2][SP-18] | 47 | TAGCCGGGACGCTT AATGCGGTTAAC |
| S35C610-2a | Cal Fluor Red 610 | 113 | AGGACCC | 29 | CGGGCGCTGGTGTCGGCA | 122 | GGGTCCT | [BHQ2][SP-18] | 47 | TAGCCGGGACGCTT AATGCGGTTAAC |
| S35C610-3a | Cal Fluor Red 610 | 114 | AGGGCCC | 29 | CGGGCGCTGGTGTCGGCA | 124 | GGGGCCCT | [BHQ2][SP-18] | 47 | TAGCCGGGACGCTT AATGCGGTTAAC |
| S35C610-3b | Cal Fluor Red 610 | 114 | AGGGCCC | 39 | CAGGGGCTGGTGTCGGCA | 124 | GGGGCCCT | [BHQ2][SP-18] | 47 | TAGCCGGGACGCTT AATGCGGTTAAC |
| S35C610-4b | Cal Fluor Red 610 | 118 | AAGGGCCC | 39 | CAGGGGCTGGTGTCGGCA | 129 | GGGGCCCTT | [BHQ2][SP-18] | 47 | TAGCCGGGACGCTT AATGCGGTTAAC |
| S35C610-5b | Cal Fluor Red 610 | 119 | AAGGTGCCC | 39 | CAGGGGCTGGTGTCGGCA | 130 | GGGCACCTT | [BHQ2][SP-18] | 47 | TAGCCGGGACGCTT AATGCGGTTAAC |
| S35FAM-3a | Fluorescein (6-FAM) | 114 | AGGGCCC | 29 | CGGGCGCTGGTGTCGGCA | 124 | GGGGCCCT | [BHQ1][SP-18] | 47 | TAGCCGGGACGCTT AATGCGGTTAAC |
| S35Q670-2a | Quasar 670 | 113 | AGGACCC | 29 | CGGGCGCTGGTGTCGGCA | 122 | GGGTCCT | [BHQ2][SP-18] | 47 | TAGCCGGGACGCTT AATGCGGTTAAC |
| S35TEX1 | Texas Red | 112 | AGGGACCC | 13 | TGCCGACACCAGCGCCCG | 121 | GGGTCCC | [DabdT][HEG] | 47 | TAGCCGGGACGCTT AATGCGGTTAAC |
| S35TEX1a | Texas Red | 112 | AGGGACCC | 21 | CCGACACCAGCGCCCG | 121 | GGGTCCC | [DabdT][HEG] | 47 | TAGCCGGGACGCTT AATGCGGTTAAC |
| S35TEX2 | Texas Red | 113 | AGGACCC | 13 | TGCCGACACCAGCGCCCG | 123 | GGGTCC | [DabdT][HEG] | 47 | TAGCCGGGACGCTT AATGCGGTTAAC |
| S35TEX2b | Texas Red | 113 | AGGACCC | 37 | CGGGCGCTGGTGTCG | 123 | GGGTCC | [Dab-dT][Sp-C18] | 47 | TAGCCGGGACGCTT AATGCGGTTAAC |
| S35TEX2c | Texas Red | 113 | AGGACCC | 38 | CGGGCGCTGGT | 123 | GGGTCC | [Dab-dT][Sp-C18] | 47 | TAGCCGGGACGCTT AATGCGGTTAAC |
| S35TEX3 | Texas Red | 114 | AGGGCCC | 13 | TGCCGACACCAGCGCCCG | 125 | GGGGCCC | [DabdT][HEG] | 47 | TAGCCGGGACGCTT AATGCGGTTAAC |
| S35TEX3a | Texas Red | 114 | AGGGCCC | 29 | CGGGCGCTGGTGTCGGCA | 125 | GGGGCCC | [DabdT][HEG] | 47 | TAGCCGGGACGCTT AATGCGGTTAAC |

FIG. 1A

| Primer-Probe Complex | 5' Mod-ification | 5' Stem SEQ ID | 5' Stem Sequence | Probe (Loop) SEQ ID | Probe (Loop) Sequence | 3' Stem SEQ ID | 3' Stem Sequence | Internal Modification | Primer SEQ ID | Primer Sequence |
|---|---|---|---|---|---|---|---|---|---|---|
| S35TEX3a | Cy5 | 114 | AGGGCCCC | 29 | CGGGCGCTGGTGTCGGCA | 124 | GGGGCCCT | [BHQ2][HEG] | 47 | TAGCCCGGGACGCTT AATGCGGTTAAC |
| S35TEX-3a | Texas Red | 114 | AGGGCCCC | 29 | CGGGCGCTGGTGTCGGCA | 124 | GGGGCCCT | [BHQ2][SP-18] | 47 | TAGCCGGGACGCTT AATGCGGTTAAC |
| S761aC610-4d | Cal Fluor Red 610 | 116 | ACGGCCGC | 90 | CGCGTCAATGACCCTGAGCG ACGTGAAA | 127 | GCGGCCGT | [BHQ2][SP-18] | 111 | CTTTACCGCTTCCAG GGTGCCTGAA |
| S761bC610-4g | Cal Fluor Red 610 | 116 | ACGGCCGC | 93 | CGCGCCAATGACCATAAGCG ACGTGAAA | 127 | GCGGCCGT | [BHQ2][SP-18] | 110 | TTTTACCGCGTCCAG TGTGCCTGAA |
| S761bC610-5g | Cal Fluor Red 610 | 117 | ACGGACCGC | 93 | CGCGCCAATGACCATAAGCG ACGTGAAA | 128 | GCGGTCCGT | [BHQ2][SP-18] | 110 | TTTTACCGCGTCCAG TGTGCCTGAA |
| S761C610-3 | Cal Fluor Red 610 | 114 | AGGGCCCC | 62 | CCTAAGGGACGGGAAAAAAT | 124 | GGGGCCCT | [BHQ2][SP-18] | 102 | CTTTACCGCTTCCAG TGTGCCTGAA |
| S761C610-3a | Cal Fluor Red 610 | 114 | AGGGCCCC | 80 | CGCGCCAATGATCCTAAGCGA CGGGAAA | 124 | GGGGCCCT | [BHQ2][SP-18] | 102 | CTTTACCGCTTCCAG TGTGCCTGAA |
| S761C610-3b | Cal Fluor Red 610 | 114 | AGGGCCCC | 88 | GCCGTAAGACGCGCCAATGA TCCTAAGCGACGGGAAAA | 124 | GGGGCCCT | [BHQ2][SP-18] | 102 | CTTTACCGCTTCCAG TGTGCCTGAA |
| S761C610-3c | Cal Fluor Red 610 | 114 | AGGGCCCC | 89 | GCCAATGATCCTAAGCGACG GGAAA | 124 | GGGGCCCT | [BHQ2][SP-18] | 102 | CTTTACCGCTTCCAG TGTGCCTGAA |
| S761C610-4c | Cal Fluor Red 610 | 115 | AGGCGCCG | 89 | GCCAATGATCCTAAGCGACG GGAAA | 126 | CGGCGCCT | [BHQ2][SP-18] | 102 | CTTTACCGCTTCCAG TGTGCCTGAA |
| S761C610-4d | Cal Fluor Red 610 | 116 | ACGGCCGC | 90 | CGCGTCAATGACCCTGAGCG ACGTGAAA | 127 | GCGGCCGT | [BHQ2][SP-18] | 102 | CTTTACCGCTTCCAG TGTGCCTGAA |
| S761C610-4e | Cal Fluor Red 610 | 116 | ACGGCCGC | 91 | CCGTTCGACGCGTCAATGACC CTGAGCGACGTGAAAA | 127 | GCGGCCGT | [BHQ2][SP-18] | 102 | CTTTACCGCTTCCAG TGTGCCTGAA |

FIG. 1B

| Primer-Probe Complex | 5' Mod-ification | 5' Stem SEQ ID | 5' Stem Sequence | Probe (Loop) SEQ ID | Probe (Loop) Sequence | 3' Stem SEQ ID | 3' Stem Sequence | Internal Modification | Primer SEQ ID | Primer Sequence |
|---|---|---|---|---|---|---|---|---|---|---|
| S761C610-4f | Cal Fluor Red 610 | 116 | ACGGCCGC | 92 | GTCAATGACCCTGAGCGACGT GAAA | 127 | GCGGCCGT | [BHQ2][SP-18] | 102 | CTTTACCGCTTCCAG TGTGGCCTGAA |
| S761C610-4g | Cal Fluor Red 610 | 116 | ACGGCCGC | 93 | CGCGCCAATGACCATAAGCG ACGTGAAA | 127 | GCGGCCGT | [BHQ2][SP-18] | 102 | CTTTACCGCTTCCAG TGTGGCCTGAA |
| S761C610-5f | Cal Fluor Red 610 | 117 | ACGGACCGC | 92 | GTCAATGACCCTGAGCGACGT GAAA | 128 | GCGGTCCGT | [BHQ2][SP-18] | 102 | CTTTACCGCTTCCAG TGTGGCCTGAA |
| S761C610-5g | Cal Fluor Red 610 | 117 | ACGGACCGC | 93 | CGCGCCAATGACCATAAGCG ACGTGAAA | 128 | GCGGTCCGT | [BHQ2][SP-18] | 102 | CTTTACCGCTTCCAG TGTGGCCTGAA |
| SB35C610 | Cal Fluor Red 610 | | | 29 | CGGGGCGTGGTGTCGGCA | | | [SP-18] | 47 | TAGCCGGGACGCTT AATGCGGTTAAC |
| SB761C610 | Cal Fluor Red 610 | | | 90 | CGCGTCAATGACCCTGAGCG ACGTGAAA | | | [SP-18] | 102 | CTTTACCGCTTCCAG TGTGGCCTGAA |
| SB761C610-g | Cal Fluor Red 610 | | | 93 | CGCGCCAATGACCATAAGCG ACGTGAAA | | | [SP-18] | 102 | CTTTACCGCTTCCAG TGTGGCCTGAA |
| S4219EC5603b | Cal Fluor Orange 560 | 132 | AGGCGCC | 133 | CAGACGACCGCGCCGCT | 134 | GGGCCT | [BHQ1][SP-18] | 135 | GAGCATAGTTATTAATA GCAGACACTCTATGCCT GTGTG |

SEQUENCE LISTING

<160> NUMBER OF SEQ ID NOS: 136

<210> SEQ ID NO 1
<211> LENGTH: 38
<212> TYPE: DNA
<213> ORGANISM: Artificial Sequence
<220> FEATURE:
<223> OTHER INFORMATION: Primer/Probe Binding Site

<400> SEQUENCE: 1
gcatgttagc cgggacgctt aatgcggtta acgccatg              38

<210> SEQ ID NO 2
<211> LENGTH: 30
<212> TYPE: DNA
<213> ORGANISM: Artificial Sequence
<220> FEATURE:
<223> OTHER INFORMATION: Primer/Probe Binding Site

<400> SEQUENCE: 2
acgccatgcc gacaccagcg cccgccagcg                                          30

<210> SEQ ID NO 3
<211> LENGTH: 38
<212> TYPE: DNA
<213> ORGANISM: Artificial Sequence
<220> FEATURE:
<223> OTHER INFORMATION: Primer/Probe Binding Site

<400> SEQUENCE: 3
aaataattca ggccacactg gaagcggtaa agacctat                                 38

<210> SEQ ID NO 4
<211> LENGTH: 47
<212> TYPE: DNA
<213> ORGANISM: Artificial Sequence
<220> FEATURE:
<223> OTHER INFORMATION: Primer/Probe Binding Site

<400> SEQUENCE: 4
dycgtwmgrc gcgycaatga ycmtragcga cgkgaaaaaa twattca                       47

<210> SEQ ID NO 5
<211> LENGTH: 47
<212> TYPE: DNA
<213> ORGANISM: Artificial Sequence
<220> FEATURE:
<223> OTHER INFORMATION: Primer/Probe Binding Site

<400> SEQUENCE: 5
gccgtaagac gcgccaatga tcctaagcga cgggaaaaaa taattca                       47

<210> SEQ ID NO 6
<211> LENGTH: 30
<212> TYPE: DNA
<213> ORGANISM: Artificial Sequence
<220> FEATURE:
<223> OTHER INFORMATION: Primer/Probe Sequence

<400> SEQUENCE: 6
acgccatgcc gacaccagcg cccgccagcg                                          30

<210> SEQ ID NO 7
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 7
acgccatgcc gacaccag                                                       18

<210> SEQ ID NO 8
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 8
cgccatgccg acaccagc                                                       18

<210> SEQ ID NO 9
<211> LENGTH: 18
<212> TYPE: DNA
<213> ORGANISM: Artificial Sequence

```
<220> FEATURE:
<223> OTHER INFORMATION: Primer/Probe Sequence

<400> SEQUENCE: 9
gccatgccga caccagcg                                                 18

<210> SEQ ID NO 10
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 10
ccatgccgac accagcgc                                                 18

<210> SEQ ID NO 11
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 11
catgccgaca ccagcgcc                                                 18

<210> SEQ ID NO 12
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 12
atgccgacac cagcgccc                                                 18

<210> SEQ ID NO 13
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 13
tgccgacacc agcgcccg                                                 18

<210> SEQ ID NO 14
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 14
gccgacacca gcgcccgc                                                 18

<210> SEQ ID NO 15
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 15
ccgacaccag cgcccgcc                                                 18
```

```
<210> SEQ ID NO 16
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 16
cgacaccagc gcccgcca                                           18

<210> SEQ ID NO 17
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 17
gacaccagcg cccgccag                                           18

<210> SEQ ID NO 18
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 18
acaccagcgc ccgccagc                                           18

<210> SEQ ID NO 19
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 19
caccagcgcc cgccagcg                                           18

<210> SEQ ID NO 20
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 20
ccgacaccag cgcc                                               14

<210> SEQ ID NO 21
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 21
ccgacaccag cgcccg                                             16

<210> SEQ ID NO 22
<211> LENGTH: 30
<212> TYPE: DNA
<213> ORGANISM: Artificial Sequence
<220> FEATURE:
<223> OTHER INFORMATION: Primer/Probe Sequence
```

<400> SEQUENCE: 22
cgctggcggg cgctggtgtc ggcatggcgt                                        30

<210> SEQ ID NO 23
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 23
cgctggcggg cgctggtg                                                     18

<210> SEQ ID NO 24
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 24
gctggcgggc gctggtgt                                                     18

<210> SEQ ID NO 25
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 25
ctggcgggcg ctggtgtc                                                     18

<210> SEQ ID NO 26
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 26
tggcgggcgc tggtgtcg                                                     18

<210> SEQ ID NO 27
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 27
ggcgggcgct ggtgtcgg                                                     18

<210> SEQ ID NO 28
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 28
gcgggcgctg gtgtcggc                                                     18

<210> SEQ ID NO 29

<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 29
cgggcgctgg tgtcggca                                            18

<210> SEQ ID NO 30
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 30
gggcgctggt gtcggcat                                            18

<210> SEQ ID NO 31
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 31
ggcgctggtg tcggcatg                                            18

<210> SEQ ID NO 32
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 32
gcgctggtgt cggcatgg                                            18

<210> SEQ ID NO 33
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 33
cgctggtgtc ggcatggc                                            18

<210> SEQ ID NO 34
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 34
gctggtgtcg gcatggcg                                            18

<210> SEQ ID NO 35
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 35
ctggtgtcgg catggcgt                                              18

<210> SEQ ID NO 36
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 36
ggcgctggtg tcgg                                                  14

<210> SEQ ID NO 37
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 37
cgggcgctgg tgtcg                                                 15

<210> SEQ ID NO 38
<211> LENGTH: 11
<212> TYPE: DNA
<213> ORGANISM: Artificial Sequence
<220> FEATURE:
<223> OTHER INFORMATION: Primer/Probe Sequence

<400> SEQUENCE: 38
cgggcgctgg t                                                     11

<210> SEQ ID NO 39
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 39
caggggctgg tgtcggca                                              18

<210> SEQ ID NO 40
<211> LENGTH: 38
<212> TYPE: DNA
<213> ORGANISM: Artificial Sequence
<220> FEATURE:
<223> OTHER INFORMATION: Primer/Probe Sequence

<400> SEQUENCE: 40
ggatgttagc cgggacgctt aatgcggtta acgccatg                        38

<210> SEQ ID NO 41
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 41
ggatgttagc cgggacgctt aatgcg                                     26

<210> SEQ ID NO 42
<211> LENGTH: 26
<212> TYPE: DNA

<213> ORGANISM: Artificial Sequence
<220> FEATURE:
<223> OTHER INFORMATION: Primer/Probe Sequence

<400> SEQUENCE: 42
gatgttagcc gggacgctta atgcgg          26

<210> SEQ ID NO 43
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 43
atgttagccg ggacgcttaa tgcggt          26

<210> SEQ ID NO 44
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 44
tgttagccgg gacgcttaat gcggtt          26

<210> SEQ ID NO 45
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 45
gttagccggg acgcttaatg cggtta          26

<210> SEQ ID NO 46
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 46
ttagccggga cgcttaatgc ggttaa          26

<210> SEQ ID NO 47
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 47
tagccgggac gcttaatgcg gttaac          26

<210> SEQ ID NO 48
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 48
agccgggacg cttaatgcgg ttaacg          26

<210> SEQ ID NO 49
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 49
gccgggacgc ttaatgcggt taacgc                                          26

<210> SEQ ID NO 50
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 50
ccgggacgct taatgcggtt aacgcc                                          26

<210> SEQ ID NO 51
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 51
cgggacgctt aatgcggtta acgcca                                          26

<210> SEQ ID NO 52
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 52
gggacgctta atgcggttaa cgccat                                          26

<210> SEQ ID NO 53
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 53
ggacgcttaa tgcggttaac gccatg                                          26

<210> SEQ ID NO 54
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 54
ggacgcttaa tgcg                                                       14

<210> SEQ ID NO 55
<211> LENGTH: 32
<212> TYPE: DNA
<213> ORGANISM: Artificial Sequence
<220> FEATURE:

```
<223> OTHER INFORMATION: Primer/Probe Sequence

<400> SEQUENCE: 55
aatgatccta agcgacggga aaaataatt ca                                    32

<210> SEQ ID NO 56
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 56
aatgatccta agcgacggga                                                 20

<210> SEQ ID NO 57
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 57
atgatcctaa gcgacgggaa                                                 20

<210> SEQ ID NO 58
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 58
tgatcctaag cgacgggaaa                                                 20

<210> SEQ ID NO 59
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 59
gatcctaagc gacgggaaaa                                                 20

<210> SEQ ID NO 60
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 60
atcctaagcg acgggaaaaa                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 61
tcctaagcga cgggaaaaaa                                                 20
```

```
<210> SEQ ID NO 62
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 62
cctaagcgac gggaaaaaat                                         20

<210> SEQ ID NO 63
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 63
ctaagcgacg ggaaaaaata                                         20

<210> SEQ ID NO 64
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 64
taagcgacgg gaaaaaataa                                         20

<210> SEQ ID NO 65
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 65
aagcgacggg aaaaaataat                                         20

<210> SEQ ID NO 66
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 66
agcgacggga aaaataatt                                          20

<210> SEQ ID NO 67
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 67
gcgacgggaa aaataattc                                          20

<210> SEQ ID NO 68
<211> LENGTH: 20
<212> TYPE: DNA
<213> ORGANISM: Artificial Sequence
<220> FEATURE:
<223> OTHER INFORMATION: Primer/Probe Sequence
```

```
<400> SEQUENCE: 68
cgacgggaaa aaataattca                                           20

<210> SEQ ID NO 69
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 69
agcgacggga aaaataatc                                            20

<210> SEQ ID NO 70
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 70
gcgacgggaa aaataatcc                                            20

<210> SEQ ID NO 71
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 71
cgacgggaaa aaataatcca                                           20

<210> SEQ ID NO 72
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 72
taagcgacgg gaaaaa                                               16

<210> SEQ ID NO 73
<211> LENGTH: 40
<212> TYPE: DNA
<213> ORGANISM: Artificial Sequence
<220> FEATURE:
<223> OTHER INFORMATION: Primer/Probe Sequence

<400> SEQUENCE: 73
gtaagacgcg ccaatgatcc taagcgacgg gaaaaaataa                     40

<210> SEQ ID NO 74
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 74
gtaagacgcg ccaatgatcc taagcgac                                  28

<210> SEQ ID NO 75
<211> LENGTH: 28
```

<210> SEQ ID NO 75
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 75
taagacgcgc caatgatcct aagcgacg                                           28

<210> SEQ ID NO 76
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 76
aagacgcgcc aatgatccta agcgacgg                                           28

<210> SEQ ID NO 77
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 77
agacgcgcca atgatcctaa gcgacggg                                           28

<210> SEQ ID NO 78
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 78
gacgcgccaa tgatcctaag cgacggga                                           28

<210> SEQ ID NO 79
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 79
acgcgccaat gatcctaagc gacgggaa                                           28

<210> SEQ ID NO 80
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 80
cgcgccaatg atcctaagcg acgggaaa                                           28

<210> SEQ ID NO 81
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 81
gcgccaatga tcctaagcga cgggaaaa                                              28

<210> SEQ ID NO 82
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 82
cgccaatgat cctaagcgac gggaaaaa                                              28

<210> SEQ ID NO 83
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 83
gccaatgatc ctaagcgacg ggaaaaaa                                              28

<210> SEQ ID NO 84
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 84
ccaatgatcc taagcgacgg gaaaaaat                                              28

<210> SEQ ID NO 85
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 85
caatgatcct aagcgacggg aaaaaata                                              28

<210> SEQ ID NO 86
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 86
aatgatccta agcgacggga aaaataa                                               28

<210> SEQ ID NO 87
<211> LENGTH: 24
<212> TYPE: DNA
<213> ORGANISM: Artificial Sequence
<220> FEATURE:
<223> OTHER INFORMATION: Primer/Probe Sequence

<400> SEQUENCE: 87
cgccaatgat cctaagcgac ggga                                                  24

<210> SEQ ID NO 88
<211> LENGTH: 39
<212> TYPE: DNA
<213> ORGANISM: Artificial Sequence

```
<220> FEATURE:
<223> OTHER INFORMATION: Primer/Probe Sequence

<400> SEQUENCE: 88
gccgtaagac gcgccaatga tcctaagcga cgggaaaaa                              39

<210> SEQ ID NO 89
<211> LENGTH: 25
<212> TYPE: DNA
<213> ORGANISM: Artificial Sequence
<220> FEATURE:
<223> OTHER INFORMATION: Primer/Probe Sequence

<400> SEQUENCE: 89
gccaatgatc ctaagcgacg ggaaa                                             25

<210> SEQ ID NO 90
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 90
cgcgtcaatg accctgagcg acgtgaaa                                          28

<210> SEQ ID NO 91
<211> LENGTH: 38
<212> TYPE: DNA
<213> ORGANISM: Artificial Sequence
<220> FEATURE:
<223> OTHER INFORMATION: Primer/Probe Sequence

<400> SEQUENCE: 91
ccgttcgacg cgtcaatgac cctgagcgac gtgaaaaa                               38

<210> SEQ ID NO 92
<211> LENGTH: 25
<212> TYPE: DNA
<213> ORGANISM: Artificial Sequence
<220> FEATURE:
<223> OTHER INFORMATION: Primer/Probe Sequence

<400> SEQUENCE: 92
gtcaatgacc ctgagcgacg tgaaa                                             25

<210> SEQ ID NO 93
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 93
cgcgccaatg accataagcg acgtgaaa                                          28

<210> SEQ ID NO 94
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 94
aatgaccctg agcgacgtg                                                    19
```

<210> SEQ ID NO 95
<211> LENGTH: 38
<212> TYPE: DNA
<213> ORGANISM: Artificial Sequence
<220> FEATURE:
<223> OTHER INFORMATION: Primer/Probe Sequence

<400> SEQUENCE: 95
ataggtcttt accgcttcca gtgtggcctg aattattt                                38

<210> SEQ ID NO 96
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 96
ataggtcttt accgcttcca gtgtgg                                             26

<210> SEQ ID NO 97
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 97
taggtcttta ccgcttccag tgtggc                                             26

<210> SEQ ID NO 98
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 98
aggtctttac cgcttccagt gtggcc                                             26

<210> SEQ ID NO 99
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 99
ggtctttacc gcttccagtg tggcct                                             26

<210> SEQ ID NO 100
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 100
gtctttaccg cttccagtgt ggcctg                                             26

<210> SEQ ID NO 101
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 101
tctttaccgc ttccagtgtg gcctga                                              26

<210> SEQ ID NO 102
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 102
ctttaccgct tccagtgtgg cctgaa                                              26

<210> SEQ ID NO 103
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 103
tttaccgctt ccagtgtggc ctgaat                                              26

<210> SEQ ID NO 104
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 104
ttaccgcttc cagtgtggcc tgaatt                                              26

<210> SEQ ID NO 105
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 105
taccgcttcc agtgtggcct gaatta                                              26

<210> SEQ ID NO 106
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 106
accgcttcca gtgtggcctg aattat                                              26

<210> SEQ ID NO 107
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 107
ccgcttccag tgtggcctga attatt                                              26

<210> SEQ ID NO 108

```
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 108
cgcttccagt gtggcctgaa ttattt                                              26

<210> SEQ ID NO 109
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 109
cgcttccagt gtgg                                                           14

<210> SEQ ID NO 110
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 110
ttttaccgcg tccagtgtgg cctgaa                                              26

<210> SEQ ID NO 111
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 111
ctttaccgct tccagggtgg cctgaa                                              26

<210> SEQ ID NO 112
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 112 agggaccc                                                                   8

<210> SEQ ID NO 113
<211> LENGTH: 7
<212> TYPE: DNA
<213> ORGANISM: Artificial Sequence
<220> FEATURE:
<223> OTHER INFORMATION: Self-Complementary Stem Sequence

<400> SEQUENCE: 113 aggaccc                                                                    7

<210> SEQ ID NO 114
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 114
```

```
agggcccc                                                              8

<210> SEQ ID NO 115
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 115 aggcgccg                                                              8

<210> SEQ ID NO 116
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 116 acggccgc                                                              8

<210> SEQ ID NO 117
<211> LENGTH: 9
<212> TYPE: DNA
<213> ORGANISM: Artificial Sequence
<220> FEATURE:
<223> OTHER INFORMATION: Self-Complementary Stem Sequence

<400> SEQUENCE: 117 acggaccgc                                                             9

<210> SEQ ID NO 118
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 118 aagggccc                                                              8

<210> SEQ ID NO 119
<211> LENGTH: 9
<212> TYPE: DNA
<213> ORGANISM: Artificial Sequence
<220> FEATURE:
<223> OTHER INFORMATION: Self-Complementary Stem Sequence

<400> SEQUENCE: 119 aaggtgccc                                                             9

<210> SEQ ID NO 120
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 120 gggtccct                                                              8

<210> SEQ ID NO 121
<211> LENGTH: 7
<212> TYPE: DNA
```

```
<213> ORGANISM: Artificial Sequence
<220> FEATURE:
<223> OTHER INFORMATION: Self-Complementary Stem Sequence

<400> SEQUENCE: 121 gggtccc                                                                 7

<210> SEQ ID NO 122
<211> LENGTH: 7
<212> TYPE: DNA
<213> ORGANISM: Artificial Sequence
<220> FEATURE:
<223> OTHER INFORMATION: Self-Complementary Stem Sequence

<400> SEQUENCE: 122 gggtcct                                                                 7

<210> SEQ ID NO 123
<211> LENGTH: 6
<212> TYPE: DNA
<213> ORGANISM: Artificial Sequence
<220> FEATURE:
<223> OTHER INFORMATION: Self-Complementary Stem Sequence

<400> SEQUENCE: 123 gggtcc                                                                  6

<210> SEQ ID NO 124
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 124 ggggccct                                                                8

<210> SEQ ID NO 125
<211> LENGTH: 7
<212> TYPE: DNA
<213> ORGANISM: Artificial Sequence
<220> FEATURE:
<223> OTHER INFORMATION: Self-Complementary Stem Sequence

<400> SEQUENCE: 125 ggggccc                                                                 7

<210> SEQ ID NO 126
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 126 cggcgcct                                                                8

<210> SEQ ID NO 127
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 127 gcggccgt                                                                8
```

-continued

<210> SEQ ID NO 128
<211> LENGTH: 9
<212> TYPE: DNA
<213> ORGANISM: Artificial Sequence
<220> FEATURE:
<223> OTHER INFORMATION: Self-Complementary Stem Sequence

<400> SEQUENCE: 128 gcggtccgt                                                                9

<210> SEQ ID NO 129
<211> LENGTH: 8
<212> TYPE: DNA
<213> ORGANISM: Artificial Sequence
<220> FEATURE:
<223> OTHER INFORMATION: Self-Complementary Stem Sequence

<400> SEQUENCE: 129 gggccctt                                                                 8

<210> SEQ ID NO 130
<211> LENGTH: 9
<212> TYPE: DNA
<213> ORGANISM: Artificial Sequence
<220> FEATURE:
<223> OTHER INFORMATION: Self-Complementary Stem Sequence

<400> SEQUENCE: 130 gggcacctt                                                                9

<210> SEQ ID NO 131
<211> LENGTH: 146
<212> TYPE: DNA
<213> ORGANISM: Artificial Sequence
<220> FEATURE:
<223> OTHER INFORMATION: Synthetic Positive Control Target Sequence

<400> SEQUENCE: 131
gagcatagtt attaatagca gacactctat gcctgtgtgg agtagcggcg gcggtcgtct        60
gtataaaggt tacagaatat ttttccataa ttttcttgta tagcagtgca gcttttcct       120 ttgtggtgta aatagcaaag caagca                                           146

<210> SEQ ID NO 132
<211> LENGTH: 7
<212> TYPE: DNA
<213> ORGANISM: Artificial Sequence
<220> FEATURE:
<223> OTHER INFORMATION: Self-Complementary Stem Sequence

<400> SEQUENCE: 132 aggcgcc                                                                  7

<210> SEQ ID NO 133
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 133
cagacgaccg ccgccgct                                                     18

<210> SEQ ID NO 134

```
<211> LENGTH: 7
<212> TYPE: DNA
<213> ORGANISM: Artificial Sequence
<220> FEATURE:
<223> OTHER INFORMATION: Self-Complementary Stem Sequence

<400> SEQUENCE: 134 ggcgcct                                                                    7

<210> SEQ ID NO 135
<211> LENGTH: 39
<212> TYPE: DNA
<213> ORGANISM: Artificial Sequence
<220> FEATURE:
<223> OTHER INFORMATION: Primer/Probe Sequence

<400> SEQUENCE: 135
gagcatagtt attaatagca gacactctat gcctgtgtg                                 39

<210> SEQ ID NO 136
<211> LENGTH: 38
<212> TYPE: DNA
<213> ORGANISM: Artificial Sequence
<220> FEATURE:
<223> OTHER INFORMATION: Primer/Probe Sequence

<400> SEQUENCE: 136
tgcttgcttt gctatttaca ccacaaagga aaaagctg                                  38
```

SEQUENCES AND THEIR USE FOR DETECTION OF SALMONELLA

CROSS-REFERENCE TO RELATED APPLICATIONS

This application claims the benefit of U.S. Provisional Application No. 61/557,469, filed Nov. 9, 2011, the contents of which are herein incorporated by reference in their entirety.

FIELD OF INVENTION

This invention relates to a rapid method for detection of *Salmonella* in a sample based on the presence of nucleic acid sequences, in particular, to a PCR-based method for detection, and to oligonucleotide molecules and reagents and kits useful therefore. In certain embodiments, the method is employed to detect *Salmonella* in a food or water sample. The present invention further relates to isolated polynucleotides, replication compositions, and kits for carrying out the method of the present invention.

BACKGROUND OF INVENTION

*Salmonella* is a genus of rod-shaped, gram-negative bacteria that is known to cause numerous illnesses, including food poisoning and typhoid fever. *Salmonella* infections can be transferred from animals to humans and can be acquired through the ingestion of food contaminated with *Salmonella*. In infections involving entiridis-type *Salmonella*, which is responsible for food poisoning, the organism typically enters the digestive tract through ingestion. In healthy adults, *Salmonella* generally must be ingested in large numbers to cause any disease. However, in young children, ingestion of a relatively small number of bacteria has been shown to cause disease due to the increased susceptibility of this population. With regard to the course of *Salmonella* infection, the bacteria typically incubate for up to one day before symptoms of infection appear. After that incubation period, intestinal inflammation occurs, resulting in diarrhea that is often bloody. Symptoms are generally mild with no sepsis, though sepsis can occur in immunocompromised individuals. Additionally, *Salmonella* meningitis can occur in children.

Because of its mode of transmission and the seriousness of some infections, detection of *Salmonella* in samples, such as food or beverage samples, is critical to the safety of the population. As such, it is desirable to have a test for the rapid and accurate detection of *Salmonella* in a sample.

SUMMARY OF INVENTION

One aspect of this invention is a method for detecting the presence of *Salmonella* in a sample, the sample comprising nucleic acids, the method comprising (a) providing a reaction mixture comprising at least one primer and probe, wherein the primer is at least 11 nucleotides in length and the probe is at least 14 nucleotides in length, and wherein (i) the primer comprises a nucleic acid sequence capable of selectively hybridizing under stringent conditions to the sequence of SEQ ID NO: 1 or a sequence complementary thereto, and the probe comprises a nucleic acid sequence capable of selectively hybridizing under stringent conditions to the sequence of SEQ ID NO: 2 or a sequence complementary thereto; or (ii) the primer comprises a nucleic acid sequence capable of selectively hybridizing under stringent conditions to the nucleic acid sequence of SEQ ID NO: 3 or a sequence complementary thereto, and the probe comprises a nucleic acid sequence capable of selectively hybridizing under stringent conditions to the sequence of SEQ ID NO: 4 or a sequence complementary thereto; and (b) performing PCR amplification of the nucleic acids of the sample using the reaction mixture of step (a); and (c) detecting the amplification of step (b).

In certain embodiments, the reaction mixture comprises both the primer and probe of (i) and the primer and probe of (ii). In certain other embodiments the primer and probe each possess a 3' terminus and a 5' terminus, and the 3' terminus of said probe is directly or indirectly attached to the 5' terminus of the primer, thereby forming a primer-probe complex. In still further embodiments, the primer-probe complex further comprises a 5' Stem Sequence and a 3' Stem Sequence, wherein the 3' terminus of the 5' Stem Sequence is directly or indirectly attached to the 5' terminus of the probe, wherein the 5' terminus of the 3' Stem Sequence is directly or indirectly attached to the 3' terminus of the probe, and wherein the 3' terminus of the 3' Stem Sequence is directly or indirectly attached of the 5' terminus of the primer. In additional embodiments, the primer-probe complex comprises a detectable label. In further embodiments, the reaction mixture further comprises a quencher oligonucleotide capable of selectively hybridizing under stringent conditions to the probe.

In certain examples, the primer capable of selectively hybridizing to SEQ ID NO: 1 comprises a nucleic acid sequence selected from the group consisting of SEQ ID NOS: 40-54, and the probe capable of selectively hybridizing to SEQ ID NO: 2 comprises a nucleic acid sequence selected from the group consisting of SEQ ID NOS: 6-39. In other examples, the primer capable of selectively hybridizing to SEQ ID NO: 3 comprises a nucleic acid sequence selected from the group consisting of SEQ ID NOS: 95-111, and wherein said probe capable of selectively hybridizing to SEQ ID NO: 4 comprises a nucleic acid sequence selected from the group consisting of SEQ ID NOS: 55-94. In further examples, the 5' Stem Sequence comprises a nucleic acid sequence selected from the group consisting of SEQ ID NOS: 112-119, and wherein said 3' Stem Sequence comprises a nucleic acid sequence selected from the group consisting of SEQ ID NOS: 120-130.

In another aspect, the invention relates to an isolated polynucleotide comprising a polynucleotide sequence selected from the group consisting of SEQ ID NOS: 6-111. In other embodiments, the invention relates to an isolated polynucleotide, wherein the polynucleotide comprises a primer-probe complex, wherein the primer-probe complex comprises a nucleic acid primer portion and a nucleic acid probe portion, wherein the primer portion is at least 11 nucleotides in length and the probe portion is at least 14 nucleotides in length, wherein the 3' terminus of the probe portion is directly or indirectly attached to the 5' terminus of the primer portion, and wherein (i) the primer portion comprises a nucleic acid sequence capable of selectively hybridizing under stringent conditions to the sequence of SEQ ID NO: 1 or a sequence complementary thereto, and the probe portion comprises a nucleic acid sequence capable of selectively hybridizing under stringent conditions to the sequence of SEQ ID NO: 2 or a sequence complementary thereto; or (ii) the primer portion comprises a nucleic acid sequence capable of selectively hybridizing under stringent conditions to the nucleic acid sequence of SEQ ID NO: 3 or a sequence complementary thereto, and the probe portion comprises a nucleic acid sequence capable of selectively hybridizing under stringent conditions to the sequence of SEQ ID NO: 4 or a sequence complementary thereto. In certain examples, the primer portion comprises a nucleic acid sequence selected from the group consisting of SEQ ID NOS: 40-54, and/or the probe portion comprises a nucleic acid sequence selected from the group consisting of SEQ ID NOS: 6-39. In other examples, the primer portion comprises a nucleic acid sequence selected from the group consisting of SEQ ID NOS: 95-111, and/or the probe portion comprises a nucleic acid sequence selected from the group consisting of SEQ ID NOS: 55-94.

In additional embodiments, the primer-probe complex further comprises a 5' Stem Sequence and a 3' Stem Sequence, wherein the 3' terminus of the 5' Stem Sequence is directly or indirectly attached to the 5' terminus of the probe portion, wherein the 5' terminus of the 3' Stem Sequence is directly or indirectly attached to the 3' terminus of the probe portion, and wherein the 3' terminus of the 3' Stem Sequence is directly or indirectly attached of the 5' terminus of the primer portion. In certain examples, the 5' Stem Sequence comprises a nucleic acid sequence selected from the group consisting of SEQ ID NOS: 112-119, and/or the 3' Stem Sequence comprises a nucleic acid sequence selected from the group consisting of SEQ ID NOS: 120-130.

In other aspects, the invention relates to a reagent tablet or kit for detection of Salmonella in a sample.

BRIEF DESCRIPTION OF THE FIGURES

FIG. 1A-1C shows exemplary combinations of probe portions, primer portions, 5' and 3' Stem Sequences, linking moieties, and detectable labels.

SUMMARY OF THE SEQUENCES

SEQ ID NOS: 1-5 are the nucleotide sequences of portions of the Salmonella genome that are useful for detecting the presence of Salmonella in a sample. In certain examples, a primer directed toward SEQ ID NO: 1 is used in conjunction with a probe directed toward SEQ ID NO: 2. In other examples, a primer directed toward SEQ ID NO: 3 is used in conjunction with a probe directed toward SEQ ID NO: 4 or 5. In certain other examples, the primer and probe are attached so as to form a primer-probe complex, wherein the 3' terminus of the probe portion is directly or indirectly attached to the 5' terminus of the primer portion. Primers and/or probes capable of selectively hybridizing under stringent conditions to SEQ ID NO: 1 include SEQ ID NOS: 40-54. Primers and/or probes capable of selectively hybridizing under stringent conditions to SEQ ID NO: 2 include SEQ ID NOS: 6-39. Primers and/or probes capable of selectively hybridizing under stringent conditions to SEQ ID NO: 3 include SEQ ID NOS: 95-111. Primers and/or probes capable of selectively hybridizing under stringent conditions to SEQ ID NO: 4 include SEQ ID NOS: 55-94.

SEQ ID NOS: 6-39 are nucleotide sequences capable of use as primers or probes for selectively hybridizing under stringent conditions, and ultimately detecting, the sequence of SEQ ID NO: 2.

SEQ ID NOS: 40-54 are nucleotide sequences capable of use as primers or probes for selectively hybridizing under stringent conditions, and ultimately detecting, the sequence of SEQ ID NO: 1.

SEQ ID NOS: 55-94 are nucleotide sequences capable of use as primers or probes for selectively hybridizing under stringent conditions, and ultimately detecting, the sequence of SEQ ID NO: 4.

SEQ ID NOS: 95-111 are nucleotide sequences capable of use as primers or probes for selectively hybridizing under stringent conditions, and ultimately detecting, the sequence of SEQ ID NO: 3.

SEQ ID NOS: 112-119 are nucleotide sequences capable of use as a 5' Stem Sequence, for example, in conjunction with a suitable probe sequence, such as those described by SEQ ID NOS: 6-39 and 55-94. In certain examples, the 5' Stem Sequence is directly or indirectly attached to a probe sequence, such that the 3' terminus of the 5' Stem Sequence is directly or indirectly attached to the 5' terminus of the probe sequence.

SEQ ID NOS: 120-130 are nucleotide sequences capable of use as a 3' Stem Sequence, for example, in conjunction with a suitable probe sequence, such as those described by SEQ ID NOS: 6-39 and 55-94. In certain examples, the 3' Stem Sequence is directly or indirectly attached to a probe sequence and a primer sequence, such that the 5' terminus of the 3' Stem Sequence is directly or indirectly attached to the 3' terminus of the probe sequence and the 3' terminus of the 3' Stem Sequence is directly or indirectly attached to the 5' terminus of the primer sequence.

SEQ ID NO: 131 is the nucleotide sequence that comprises a synthetic SV40 ("sSV40") sequence which can be effectively employed, for example, as a target for a positive control amplification reaction. In certain embodiments, this sequence can be used as a "spiked" control and can be amplified and detected using SEQ ID NOS: 132-136.

SEQ ID NOS: 132-136 are nucleotide sequences useful for amplifying and detecting the Positive Control sequence of SEQ ID NO: 131. In certain embodiments, SEQ ID NO: 132 is a 5' stem sequence, SEQ ID NO: 133 is a probe sequence, SEQ ID NO: 134 is a 3' stem sequence, SEQ ID NO 135 is a forward primer sequence, and SEQ ID NO: 136 is a reverse primer sequence. In other embodiments, SEQ ID NOS: 132-135 are combined so as to form a primer-probe complex capable of forming a stem-loop structure. In other embodiments that primer-probe complex is used as a forward primer/probe in conjunction with SEQ ID NO: 136 as reverse primer to amplify and detect SEQ ID NO: 131.

DETAILED DESCRIPTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

In this disclosure, a number of terms and abbreviations are used. The following definitions are provided.

As used herein, the term "about" or "approximately" means within 20%, preferably within 10%, and more preferably within 5% of a given value or range.

The term "comprising" is intended to include embodiments encompassed by the terms "consisting essentially of" and "consisting of." Similarly, the term "consisting essentially of" is intended to include embodiments encompassed by the term "consisting of."

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

The term "amplification product" or "amplicon" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition may comprise the components for nucleic acid replication, for example: nucleotide triphosphates, two (or more) primers or primer-probe complexes with appropriate sequences, thermostable polymerase, buffers, solutes, and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *Thermus aquaticus* ligase), two sets of adjacent oligonucleotides (wherein one member of each set is complementary to each of the target strands), Tris-HCl buffer, KCl, EDTA, NAD, dithiothreitol, and salmon sperm DNA. See, for example, Tabor et al., *Proc. Natl. Acad. Sci. U.S.A.* 82:1074-1078 (1985).

The term "primer" refers to an oligonucleotide (synthetic or occurring naturally) that is capable of acting as a point of initiation of nucleic acid synthesis or replication along a complementary strand when placed under conditions in which synthesis of a complementary strand is catalyzed by a polymerase. A primer can further contain a detectable label, for example a 5' end label. In certain embodiments, primers of the present invention are 8-60 nucleic acids in length. In other embodiments, primers are 10-50, 14-40, or 20-30 nucleic acids in length. In certain specific embodiments, primers are at least 10, 11, 12, 13, 14, 15, 16, 17, 18, 19, 20, 21, 22, 23, 24, 25, 26, 27, 28, 29, or 30 nucleotides in length.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest. A probe or primer-probe complex can further contain a detectable label. In certain embodiments, probes of the present invention are 8-60 nucleic acids in length. In other embodiments, probes are 10-50, 14-40, or 20-30 nucleic acids in length. In certain specific embodiments, probes are at least 10, 11, 12, 13, 14, 15, 16, 17, 18, 19, 20, 21, 22, 23, 24, 25, 26, 27, 28, 29, or nucleotides in length.

A probe can either be an independent entity or complexed with or otherwise attached to a primer, such as where a probe is connected, directly or indirectly, via its 3' terminus to a primer's 5' terminus. In some examples, the probe and primer are attached through a linker, which may be a nucleotide or non-nucleotide linker and which may be a non-amplifiable linker, such as a hexethylene glycol (HEG) or 18-carbon linker. In such a case, this would be termed a "primer-probe complex." One example of such primer-probe complexes can be found in U.S. Pat. No. 6,326,145, incorporated herein by reference in its entirety, which are frequently referred to as "Scorpion probes" or "Scorpion primers." In a typical primer probe complex, the primer portion can be, for example, at least 10, 11, 12, 13, 14, 15, 16, 17, 18, 19, 20, 21, 22, 23, 24, 25, 26, 27, 28, 29, or 30 nucleotides in length, while the probe portion can be, for example, at least 10, 11, 12, 13, 14, 15, 16, 17, 18, 19, 20, 21, 22, 23, 24, 25, 26, 27, 28, 29, or 30 nucleotides in length.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher.

The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter.

As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Preferably, the reporter may be selected from fluorescent organic dyes modified with a suitable linking group for attachment to the oligonucleotide, such as to the terminal 3' carbon or terminal 5' carbon. The quencher may also be selected from organic dyes, which may or may not be fluorescent, depending on the embodiment of the present invention. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, Handbook of Fluorescent Probes and Research Chemicals, Molecular Probes of Eugene, Oreg., 1992, the content of which is incorporated herein by reference.

Preferred reporter-quencher pairs may be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another preferred group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Most preferably, the reporters and quenchers are selected from fluorescein and rhodamine dyes. These dyes and appropriate linking methodologies for attachment to oligonucleotides are well known in the art.

Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

One example of a probe that contains a reporter and a quencher is a Scorpion probe in either a unimolecular or bimolecular conformation. In a unimolecular Scorpion, the probe portion of the primer-probe complex is flanked by self-complementary regions, which allow the probe to form into a stem-loop structure when the probe is unbound from its target DNA. In certain embodiments, these are termed the 5' Stem Sequence, which has its 3' terminus attached to the 5' terminus of the probe, and the 3' Stem Sequence, which has its 5' terminus attached to the 3' terminus of the probe and its 3' terminus attached to the primer. These attachments can be either direct or indirect, such as through a linker. Further, in a unimolecular Scorpion, a reporter is typically attached at or near one of the self-complementary regions, such as at the 5' terminus of the Scorpion probe, and a quencher is attached at or near the other self-complementary region, such as immediately 5' to the non-amplifiable linker, such that the quencher is in sufficiently close proximity to the reporter to cause quenching when the probe is in its stem-loop conformation. In a bimolecular Scorpion, self-complementary flanking regions are not typically employed, but rather a separate "blocking oligonucleotide" or "quenching oligonucleotide" is employed in conjunction with the Scorpion probe. This blocking oligonucleotide is capable of hybridizing to the probe region of the Scorpion probe when the probe is unbound from its target DNA. Further, in a bimolecular Scorpion, the reporter is typically attached to the probe region of the Scorpion probe, such as at the 5' terminus of the Scorpion probe, while the quencher is attached to the blocking oligonucleotide, such as at the 3' terminus of the blocking oligonucleotide, such that the quencher is in sufficiently close proximity to the reporter to cause quenching when the probe is unbound from its target DNA and is instead hybridized to the blocking oligonucleotide.

Another example of a probe that contains a reporter and a quencher is a probe that is to be used in a 5'-exonuclease assay, such as the TaqMan® real-time PCR technique. In this context, the oligonucleotide probe will have a sufficient number of phosphodiester linkages adjacent to its 5' end so that the 5' to 3' nuclease activity employed can efficiently degrade the bound probe to separate the reporters and quenchers. Yet another example of a probe that contains a reporter and quencher is a Molecular Beacon type probe, which contains a probe region flanked by self-complementary regions that allow the probe to form a stem-loop structure when unbound from the probe's target sequence. Such probes typically have a reporter attached at or near one terminus and a quencher attached at or near the other terminus such that the quencher is in sufficiently close proximity to the reporter to cause quenching when the probe is in its unbound, and thus stem-loop, form.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" refers to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, for example, in Sambrook, J., Fritsch, E. F. and Maniatis, T., *Molecular Cloning: A Laboratory Manual,* 2nd ed., Cold Spring Harbor Laboratory Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment, the length for a hybridizable nucleic acid is at least about 10 nucleotides. More preferably a minimum length for a hybridizable nucleic acid is at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, or, most preferably, at least 30 nucleotides. Furthermore, the skilled artisan will recognize that the temperature and wash solution salt concentration may be adjusted as necessary according to factors such as length of the probe.

In certain embodiments, primers probes are able to selectively hybridize to a target nucleic acid sequence under selective (e.g., stringent) hybridization conditions. The term "selectively hybridize" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing nucleic acid sequences typically have about at least 70% sequence identity, preferably at least 80% sequence identity, and most preferably 90%, 95%, 97%, 99%, or 100% sequence identity with each other.

Standard recombinant DNA and molecular cloning techniques used here are well known in the art and are described by, e.g., Sambrook et al. (supra); and by Ausubel, F. M. et al., *Current Protocols in Molecular Biology*, published by Greene Publishing Assoc. and Wiley-Interscience (1987).

Oligonucleotides

Methods have been developed for detecting *Salmonella* bacteria in a sample by detecting one or more target nucleic acid sequences. In certain embodiments, the methods involve isolated polynucleotides and/or reaction mixtures comprising a primer and a probe, wherein (i) the primer is capable of selectively hybridizing under stringent conditions to SEQ ID NO: 1 or a sequence complementary thereto and the probe is capable of selectively hybridizing under stringent conditions to SEQ ID NO: 2 or a sequence complementary thereto; or (ii) the primer is capable of selectively hybridizing under stringent conditions to SEQ ID NO: 3 or a sequence complementary thereto and the probe is capable of selectively hybridizing under stringent conditions to SEQ ID NO: 4 or a sequence complementary thereto. In some embodiments, probes capable of selectively hybridize to SEQ ID NO: 1 include SEQ ID NOS: 40-54. In other embodiments, primers capable of selectively hybridize to SEQ ID NO: 2 include SEQ ID NOS: 6-39. In further embodiments, probes capable of selectively hybridize to SEQ ID NO: 3 include SEQ ID NOS: 95-111. In still further embodiments, primers capable of selectively hybridize to SEQ ID NO: 4 include SEQ ID NOS: 55-94.

In some embodiments, the primer and probe are directly or indirectly attached, thereby forming a primer-probe complex. In some examples, the primer-probed complex is formed by directly or indirectly attaching 3' terminus of the probe to the 5' terminus of the primer. These primer probe complexes of the instant invention can also contain a non-amplifiable linker that connects the 3' terminus of the probe region to the 5' terminus of the primer region. This non-amplifiable linker stops extension of a complementary strand from proceeding into the probe region of the primer-probe complex. Examples of such non-amplifiable linkages include hexethylene glycol (HEG) and, preferably, 18-carbon linkers.

Primer-probe complexes of the present invention can also contain a self-complementary region, including a 3' Stem Sequence and a 5' Stem Sequence, that allows the primer-probe complex to form a stem-loop structure when the probe is unbound from its target DNA, which may be useful, for example, in bringing the reporter and quencher into sufficiently close proximity to one another to cause the reporter signal to be quenched. In some embodiments, the 5' Stem Sequence is one of SEQ ID NOS: 112-119, and the 3' Stem Sequence is one of SEQ ID NOS: 120-130.

In additional embodiments, the primers, probes, or primer-probe complexes further comprise a detectable label, such as a 5' end label or a reporter-quencher pair. In some instances, a quencher oligonucleotide can be employed with a probe or primer-probe complex, which quencher oligonucleotide is capable of hybridizing to the probe or probe region of the primer-probe complex when the probe is unbound from its target DNA. If the reporter is attached to the probe or primer-probe complex and the quencher is attached to the blocking oligonucleotide, this can bring the reporter and quencher into sufficiently close proximity to one another to allow quenching to occur.

In certain embodiments, the primer or primer-probe complex is used in conjunction with a reverse primer. In still further embodiments, two such primer-probe complexes are employed, one as a forward primer-probe complex and the other as a reverse primer-probe complex. Exemplary combinations of probe portions, primer portions, 5' and 3' Stem Sequences, linking moieties, and detectable labels are provided in FIGS. 1A-1C.

In addition to their usefulness in PCR, these primer-probe complexes may also be useful for other nucleic acid amplification methods such as the ligase chain reaction (LCR) (Backman et al., 1989, EP 0 320 308; Carrino et al., 1995, *J. Microbiol. Methods* 23: 3-20); nucleic acid sequence-based amplification (NASBA), (Carrino et al., 1995, supra); and self-sustained sequence replication (3SR) and 'Q replicase amplification' (Pfeffer et al., 1995 *Veterinary Res. Comm.* 19: 375-407).

In addition, oligonucleotides of the present invention also may be used as hybridization probes. Hybridization using DNA probes has been frequently used for the detection of pathogens in food, clinical and environmental samples, and the methodologies are generally known to one skilled in the art. It is generally recognized that the degree of sensitivity and specificity of probe hybridization is lower than that achieved through the previously described amplification techniques.

Assay Methods

Detection of the selected gene targets, and subsequent detection of the presence of *Salmonella* in a sample, may be accomplished in any suitable manner. Preferred methods are primer-directed amplification methods and nucleic acid hybridization methods. These methods may be used to detect *Salmonella* in a sample that is either a complex matrix or a purified culture, e.g., from an animal, environmental, or food source suspected of contamination.

A preferred embodiment of the instant invention comprises (1) culturing a complex sample mixture in a non-selective growth media to resuscitate the target bacteria, (2) releasing total target bacterial DNA, and (3) subjecting the total DNA to an amplification protocol with a primer and probe, or a primer-probe complex, of the invention and a reverse primer, or two primer-probe complexes of the invention (one acting as a forward primer and a second acting as a reverse primer.

Primer-Directed Amplification Assay Methods

A variety of primer-directed nucleic acid amplification methods are known in the art which can be employed in the present invention, including thermal cycling methods (e.g., PCR, RT-PCR, and LCR), as well as isothermal methods and strand displacement amplification (SDA). The preferred method is PCR. In one preferred embodiment, the primer-probe complexes set forth in FIGS. 1A-1C may be used as primers for use in primer-directed nucleic acid amplification for the detection of the target nucleic acid(s) and, ultimately, the detection of Salmonella.

Sample Preparation:

The oligonucleotides and methods according to the instant invention may be used directly with any suitable clinical or environmental samples, without any need for sample preparation. In order to achieve higher sensitivity, and in situations where time is not a limiting factor, it is preferred that the samples be pre-treated and that pre-amplification enrichment is performed.

The minimum industry standard for the detection of food-borne bacterial pathogens is a method that will reliably detect the presence of one pathogen cell in 25 g of food matrix as described in Andrews et al., 1984, "Food Sample and Preparation of Sample Homogenate", Chapter 1 in *Bacteriological Analytical Manual*, 8th Edition, Revision A, Association of Official Analytical Chemists, Arlington, Va. In order to satisfy this stringent criterion, enrichment methods and media have been developed to enhance the growth of the target pathogen cell in order to facilitate its detection by biochemical, immunological or nucleic acid hybridization means. Typical enrichment procedures employ media that will enhance the growth and health of the target bacteria and also inhibit the growth of any background or non-target microorganisms present. For example, the USDA has set forth a protocol for enrichment of samples of ground beef to be tested for pathogenic *E. coli* (U.S. Food and Drug Administration, Bacterial Analytical Manual).

Selective media have been developed for a variety of bacterial pathogens and one of skill in the art will know to select a medium appropriate for the particular organism to be enriched. A general discussion and recipes of non-selective media are described in the FDA Bacteriological Analytical Manual. (1998) published and distributed by the Association of Analytical Chemists, Suite 400, 2200 Wilson Blvd, Arlington, Va. 22201-3301.

After selective growth, a sample of the complex mixtures is removed for further analysis. This sampling procedure may be accomplished by a variety of means well known to those skilled in the art. In a preferred embodiment, 5 µl of the enrichment culture is removed and added to 200 µl of lysis solution containing protease. The lysis solution is heated at 37° C. for 20 min followed by protease inactivation at 95° C. for 10 min as described in the BAX® System User's Guide, DuPont Qualicon, Inc., Wilmington, Del.

PCR Assay Methods:

A preferred method for detecting the presence of the present invention's target nucleic acids and subsequently *Salmonella* in a sample comprises (a) performing PCR amplification using a primer and probe, or a primer-probe complex, of the present invention, such as those described in FIGS. 1A-1C, and a suitable reverse primer; and (b) detecting the amplification, whereby a positive detection of the amplification indicates the presence of *Salmonella* in the sample. In another embodiment, PCR amplification is performed using two different primer-probe complexes of the present invention that have primer binding regions that are sufficiently separated such that one primer-probe complex acts as a forward primer and the second primer-probe complex acts as a reverse primer. Looking at FIGS. 1A-1C, examples of such forward-acting primer-probe complexes include S35C610-1, S35C610-2, S35C610-2a, S35C610-3a, S35C610-3a, S35C610-3a, S35C610-3b, S35C610-4b, S35C610-5b, S35FAM-3a, S35Q670-2a, S35TEX1, S35TEX1a, S35TEX2, S35TEX2, S35TEX2b, S35TEX2c, S35TEX3, S35TEX3a, S35TEX3a, S35TEX-3a, and SB35C610, while examples of such reverse-acting primer-probe complexes include S761aC610-4d, S761bC610-4g, S761bC610-5g, S761C610-3, S761C610-3a, S761C610-3b, S761C610-3c, S761C610-4c, S761C610-4d, S761C610-4e, S761C610-4-f, S761C610-4g, S761C610-5f, S761C610-5g, SB7610610, and SB761C610-g.

In another preferred embodiment, prior to performing PCR amplification, a step of preparing the sample may be carried out. The preparing step may comprise at least one of the following processes: (1) bacterial enrichment, (2) separation of bacterial cells from the sample, (3) cell lysis, and (4) total DNA extraction.

Amplification Conditions:

A skilled person will understand that any generally acceptable PCR conditions may be used for successfully detecting the nucleic acid targets and the target *Salmonella* bacteria using the oligonucleotides of the instant invention, and depending on the sample to be tested and other laboratory conditions, routine optimization for the PCR conditions may be necessary to achieve optimal sensitivity and specificity.

Detection/Examination/Analysis:

Primer-directed amplification products produced by the methods of the present invention can be analyzed using various methods. Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture during or immediately following amplification. In addition, heterogeneous detection methods, which involve separation of amplification products during or prior to detection, can be employed in the present invention.

Homogenous detection may be employed to carry out "real-time" primer-directed nucleic acid amplification and detection, using primer-probe complexes of the instant invention (e.g., "real-time" PCR and "real-time" RT-PCR). A particularly preferred "real-time" detection method is the Scorpion probe assay as set forth in U.S. Pat. No. 6,326,145, which is hereby incorporated by reference in its entirety. In the Scorpion probe assay, PCR amplification is performed using a Scorpion probe (either unimolecular or bimolecular) as a primer-probe complex, the Scorpion probe possessing an appropriate reporter-quencher pair to allow the detectable signal of the reporter to be quenched prior to elongation of the primer. Post-elongation, the quenching effect is eliminated and the amount of signal present is quantitated. As the amount of amplification product increases, an equivalent increase in detectable signal will be observed, thus allowing the amount of amplification product present to be determined as a function of the amount of detectable signal measured. When more than one Scorpion probe is employed in a Scorpion probe assay of present invention, each probe can have the same detectable label attached or a different detectable label attached, thus allowing each probe to be detected independently of the other probes.

Another preferred "real-time" detection method is the 5'-exonuclease detection method, as set forth in U.S. Pat. Nos. 5,804,375, 5,538,848, 5,487,972, and 5,210,015, each of which is hereby incorporated by reference in its entirety. In the 5'-exonuclease detection assay, a modified probe is employed during PCR that binds intermediate to or between the two members of an amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away.

Again, when more than one TaqMan® probe is employed in a 5'-exonuclease detection assay of present invention, such as one directed to two or more of SEQ ID NOS: 686-696, each probe can have a different detectable label (e.g., reporter-quencher pair) attached, thus allowing each probe to be detected independently of the other probes.

In addition to homogenous detection methods, a variety of other heterogeneous detection methods are known in the art that can be employed in the present invention, including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Instrumentation:

When homogenous detection is employed, the level of fluorescence is preferably measured using a laser fluorometer such as, for example, an ABI Prism Model 7500 Fast Sequence Detector. However, similar detection systems for measuring the level of fluorescence in a sample are included in the invention.

Reagents and Kits:

Any suitable nucleic acid replication composition ("replication composition") in any format can be used. A typical replication composition for PCR amplification may comprise, for example, dATP, dCTP, dGTP, and dTTP; target specific primers, probes, or primer-probe complexes; and a suitable polymerase.

If the replication composition is in liquid form, suitable buffers known in the art may be used (Sambrook, J. et al., supra).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

In certain embodiments, the replication composition of the instant invention comprises at least one primer and probe and a thermostable DNA polymerase, wherein the primer is at least 10 nucleotides in length and the probe is at least 10 nucleotides in length, and wherein (i) the primer comprises a nucleic acid sequence capable of selectively hybridizing under stringent conditions to the sequence of SEQ ID NO: 1 or a sequence complementary thereto, and the probe comprises a nucleic acid sequence capable of selectively hybridizing under stringent conditions to the sequence of SEQ ID NO: 2 or a sequence complementary thereto; or (ii) the primer comprises a nucleic acid sequence capable of selectively hybridizing under stringent conditions to the nucleic acid sequence of SEQ ID NO: 3 or a sequence complementary thereto, and the probe comprises a nucleic acid sequence capable of selectively hybridizing under stringent conditions to the sequence of SEQ ID NO: 4 or a sequence complementary thereto. In certain specific embodiments, the primer is at least 11, 12, 13, 14, 15, 16, 17, 18, 19, 20, 21, 22, 23, 24, 25, 26, 27, 28, 29, or 30 nucleotides in length. In further embodiments, the probe is at least 11, 12, 13, 14, 15, 16, 17, 18, 19, 20, 21, 22, 23, 24, 25, 26, 27, 28, 29, or 30 nucleotides in length.

In some examples, the primer and probe are directly or indirectly attached, thereby forming a primer-probe complex. In other examples, the primer-probe complex involves direct or indirect attachment of the 3' terminus of the probe to the 5' terminus of the primer. In further examples, the probe portion of the primer-probe complex is flanked by a 5' Stem Sequence, such as set forth in SEQ ID NOS: 112-119, and a 3' Stem Sequence, such as set forth in SEQ ID NOS: 120-130.

In some embodiments, the primer portion capable of selectively hybridizing under stringent conditions to the sequence of SEQ ID NO: 1 comprises a nucleic acid sequence selected from the group consisting of SEQ ID NOS: 40-54. In other embodiments, the primer portion capable of selectively hybridizing under stringent conditions to the sequence of SEQ ID NO: 2 comprises a nucleic acid sequence selected from the group consisting of SEQ ID NOS: 5-39. In further embodiments, the primer portion capable of selectively hybridizing under stringent conditions to the sequence of SEQ ID NO: 3 comprises a nucleic acid sequence selected from the group consisting of SEQ ID NOS: 95-111. In still further embodiments, the primer portion capable of selectively hybridizing under stringent conditions to the sequence of SEQ ID NO: 4 comprises a nucleic acid sequence selected from the group consisting of SEQ ID NOS: 55-94.

In other specific embodiments, the replication composition of the instant invention comprises (a) at least one primer-probe complex selected from FIGS. 1A-1C, and (b) thermostable DNA polymerase. Another preferred replication composition comprises (a) at least two primer-probe complexes selected from FIGS. 1A-1C, each directed toward a different target DNA region such that one complex acts as a forward primer and the other acts as a reverse primer; and (b) thermostable DNA polymerase. In certain examples, the forward-acting primer-probe complex is selected from the group consisting of S35C610-1, S35C610-2, S35C610-2a, S35C610-

3a, S35C610-3a, S35C610-3a, S35C610-3b, S35C610-4b, S350610-5b, S35FAM-3a, S35Q670-2a, S35TEX1, S35TEX1a, S35TEX2, S35TEX2, S35TEX2b, S35TEX2c, S35TEX3, S35TEX3a, S35TEX3a, S35TEX-3a, and SB35C610, while the reverse-acting primer-probe complex is selected from the group consisting of S761aC610-4d, S761bC610-4g, S761bC610-5g, S7610610-3, S761C610-3a, S761C610-3b, S761C610-3c, S761C610-4c, S761C610-4d, S761C610-4e, S761C610-4-f, S761C610-4g, S761C610-5f, S761C610-5g, SB761C610, and SB761C610-g. In certain examples, the replication composition further comprises a suitable quencher oligonucleotide capable of binding to, and quenching the signal of, the probe portion of the primer-probe complex.

A preferred kit of the instant invention comprises any one of the above replication compositions. A preferred tablet of the instant invention comprises any one of the above replication compositions. More preferably, a kit of the instant invention comprises the foregoing preferred tablet.

In some instances, an internal positive control can be included in the reaction. The internal positive control can include control template nucleic acids (e.g. DNA or RNA), control primers, and a control nucleic acid probe. The advantages of an internal positive control contained within a PCR reaction have been previously described (U.S. Pat. No. 6,312,930 and PCT Application No. WO 97/11197, each of which is hereby incorporated by reference in its entirety), and include: (i) the control may be amplified using a single primer; (ii) the amount of the control amplification product is independent of any target DNA or RNA contained in the sample; (iii) the control DNA can be tableted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction and/or a detectable label on the control nucleic acid that is distinct from the detectable label on the nucleic acid probe directed to the target.

Control DNA will be of appropriate size and base composition to permit amplification in a primer-directed amplification reaction. The control template DNA sequence may be obtained from any suitable source, but must be reproducibly amplified under the same conditions that permit the amplification of the target amplification product.

Preferred control sequences include, for example, control primers and probes directed toward SV40 DNA.

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction, a suitable number of copies of the control DNA template must be included in each amplification reaction.

In some instances, it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed. In addition, the replication composition for either target DNA or control DNA amplification can contain a nucleic acid probe, preferably possessing a detectable label.

EXAMPLES

The present invention is further defined in the following Examples. It should be understood that these Examples, while indicating preferred embodiments of the invention, are given by way of illustration only.

Example 1

Determination of Inclusivity/Exclusivity of the Individual Targets via Scorpion® Assay Samples of organisms were analyzed to establish inclusivity and exclusivity of numerous Scorpion® probes of the present invention. For inclusivity, independent, bona fide *Salmonella* isolates were used. For exclusivity, closely related non-target organisms were used to ensure that the assay would discriminate the target organisms from other non-target organisms.

DNA Lysate Preparation

Material tested was overnight growth pure cultures of the target and non-target organisms grown at 37° C. in BHI media. Pure cultures grown overnight to cell densities of approximately $1 \times 10^9$ cfu/ml. For exclusivity, 1:10 dilutions of overnight cultures were tested. For inclusivity, overnight cultures were diluted approximately 1:10,000 into TSB. 5 μl of the material to be tested was added to 200 μl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions

30 μl of the DNA lysate was used to hydrate lyophylized PCR reaction components to obtain DNA lysate/PCR reaction component mixtures. The PCR reaction components were in the form of customized reagent containing GoTaq DNA Polymerase (Promega, Madison, Wis.), deoxynucleotides (Roche Diagnostics, Indianapolis, Ind.), BSA, and surfactamps (Sigma-Aldrich, St. Louis, Mo.). In addition, the primers and Scorpion® probes listed in Table 1 were included in the amounts provided. As this Table demonstrates, each of these Scorpion® probes was designed as a uni-molecular Scorpion®, such that its structure includes (in 5' to 3' order): a 5' fluorescent end label, 5' Stem Sequence, a probe sequence, a 3' Stem Sequence, an internal quencher, an 18-carbon non-amplifiable linker, and a primer sequence.

TABLE 1

Primers and Probes Used in Inclusivity/Exclusivity Study

| Nucleotide Name | Target | Amt. Per Rxn. | 5' End Label | 5' Stem SEQ ID NO: | Probe SEQ ID NO: | 3' Stem SEQ ID NO: | Internal Label/ Linker | Primer SEQ ID NO: |
|---|---|---|---|---|---|---|---|---|
| Forward Scorpion S35C610-3a | Salmonella | 50-150 nM | Cal Fluor Red 610 | 114 | 29 | 124 | BHQ2/ 18-Carbon Linker | 47 |
| Forward Primer 35 | Salmonella | 250-350 nM | | | | | | 47 |
| Reverse Scorpion S761C610-4d | Salmonella | 50-150 nM | Cal Fluor Red 610 | 116 | 90 | 127 | BHQ2/ 18-Carbon Linker | 111 |
| Reverse Scorpion S761C610-5g | Salmonella | 50-150 nM | Cal Fluor Red 610 | 117 | 93 | 128 | BHQ2/ 18-Carbon Linker | 102 |
| Reverse Primer 761 | Salmonella | 250-350 nM | | | | | | 111 |
| Forward Scorpion S4219EC560-3b | Positive Control (sSV40) | 10-50 nM | Cal Fluor Orange 560 | 132 | 133 | 134 | BHQ1/ 18-Carbon Linker | 135 |
| Forward Primer 4219E | Positive Control (sSV40) | 30-60 nM | | | | | | 135 |
| Reverse Primer 4313E | Positive Control (sSV40) | 70-125 nM | | | | | | 136 |

Amplification and testing were performed on the BAX® Q7 instrument (DuPont Qualicon, Wilmington, Del.). The thermal cycling conditions were as follows: 2 minutes at 95° C., followed by 46 cycles of 95° C. for 10 seconds and 70° C. for 50 seconds, with the fluorescent signal captured during the 70° C. step at each cycle.

Results

As can be seen in Tables 2-3, using Scorpion® probes, the method of the present invention was able to detect the various targets appropriately, including distinguishing between target and non-target organisms.

TABLE 2

Inclusivity Results

| DuPont Qualicon ID # | Presumptive ID | ID Species | BAX ® System Result |
|---|---|---|---|
| 584 | Salmonella typhi | Salmonella typhi | Positive |
| 585 | Salmonella typhi | Salmonella typhi | Positive |
| 586 | Salmonella typhimurium | Salmonella typhimurium | Positive |
| 706 | Salmonella enteritidis | Salmonella enteritidis | Positive |
| 707 | Salmonella newport | Salmonella newport | Positive |
| 725 | Salmonella arizonae | Salmonella arizonae | Positive |
| 726 | Salmonella arizonae | Salmonella arizonae | Positive |
| 737 | Salmonella enteritidis | Salmonella enteritidis | Positive |
| 738 | Salmonella virchow | Salmonella virchow | Positive |
| 739 | Salmonella stanley | Salmonella stanley | Positive |
| 741 | Salmonella gallinarum | Salmonella gallinarum | Positive |
| 917 | Salmonella choleraesuis | Salmonella choleraesuis | Positive |
| 918 | Salmonella paratyphi A | Salmonella paratyphi | Positive |
| 919 | Salmonella paratyphi A | Salmonella paratyphi | Positive |
| 964 | Salmonella bredeney | Salmonella bredeney | Positive |
| 966 | Salmonella napoli | Salmonella napoli | Positive |
| 1084 | Salmonella typhimurium | Salmonella typhimurium | Positive |
| 1084 | Salmonella typhimurium | Salmonella typhimurium | Positive |
| 1085 | Salmonella binza | Salmonella binza | Positive |
| 1248 | Salmonella panama | Salmonella panama | Positive |
| 1251 | Salmonella kedougou | Salmonella kedougou | Positive |
| 1255 | Salmonella montevideo | Salmonella montevideo | Positive |
| 1261 | Salmonella newport | Salmonella newport | Positive |
| 1329 | Salmonella braenderup | Salmonella braenderup | Positive |
| 1331 | Salmonella berta | Salmonella berta | Positive |
| 1332 | Salmonella anatum | Salmonella anatum | Positive |
| 1333 | Salmonella stanley | Salmonella stanley | Positive |
| 1334 | Salmonella anatum | Salmonella anatum | Positive |
| 1335 | Salmonella agona | Salmonella agona | Positive |
| 1336 | Salmonella thompson | Salmonella thompson | Positive |
| 1337 | Salmonella braenderup | Salmonella braenderup | Positive |

TABLE 2-continued

Inclusivity Results

| DuPont Qualicon ID # | Presumptive ID | ID Species | BAX ® System Result |
|---|---|---|---|
| 1338 | *Salmonella* brandenburg | *Salmonella* brandenburg | Positive |
| 1339 | *Salmonella* thompson | *Salmonella* thompson | Positive |
| 1343 | *Salmonella* blockley | *Salmonella* haardt | Positive |
| 1352 | *Salmonella* agona | *Salmonella* agona | Positive |
| 1356 | *Salmonella* bredeney | *Salmonella* bredeney | Positive |
| 1372 | *Salmonella* saintpaul | *Salmonella* saintpaul | Positive |
| 1424 | *Salmonella* manchester | *Salmonella* manchester | Positive |
| 1429 | unknown | *Salmonella* anfo | Positive |
| 1467 | *Salmonella typhimurium* | *Salmonella typhimurium* | Positive |
| 1469 | *Salmonella* ealing | *Salmonella* ealing | Positive |
| 1476 | *Salmonella* napoli | *Salmonella* napoli | Positive |
| 1480 | *Salmonella* indiana | *Salmonella* indiana | Positive |
| 1482 | *Salmonella* pullorum | *Salmonella* pullorum | Positive |
| 1491 | *Salmonella* weltevreden | *Salmonella* weltevreden | Positive |
| 1492 | *Salmonella* montevideo | *Salmonella* montevideo | Positive |
| 1507 | *Salmonella* pullorum | *Salmonella* pullorum | Positive |
| 1509 | *Salmonella* bovismorbificans | *Salmonella* bovismorbificans | Positive |
| 1510 | *Salmonella* bareilly | *Salmonella* bareilly | Positive |
| 1521 | *Salmonella* amersfoort | *Salmonella* abaetetuba | Positive |
| 1523 | *Salmonella* berkeley | *Salmonella* berkeley | Positive |
| 1525 | *Salmonella* betioky | *Salmonella* betioky | Positive |
| 1526 | *Salmonella* austin | *Salmonella* austin | Positive |
| 1527 | *Salmonella* atlanta | *Salmonella* atlanta | Positive |
| 1530 | *Salmonella* amager | *Salmonella* altendorf | Positive |
| 1531 | *Salmonella* altendorf | *Salmonella* altendorf | Positive |
| 1535 | *Salmonella* brookfield | *Salmonella* brookfield | Positive |
| 1543 | *Salmonella* adelaide | *Salmonella* adelaide | Positive |
| 1547 | *Salmonella* aberdeen | *Salmonella* species | Positive |
| 1548 | *Salmonella* abony | *Salmonella* abony | Positive |
| 1551 | *Salmonella* aequatoria | *Salmonella* species | Positive |
| 1552 | *Salmonella* alabama | *Salmonella* alabama | Positive |
| 1553 | *Salmonella* ball | *Salmonella* ball | Positive |
| 1554 | *Salmonella* banalia | *Salmonella* species | Positive |
| 1555 | *Salmonella* brancaster | *Salmonella* brancaster | Positive |
| 1556 | *Salmonella* alachua | *Salmonella* alachua | Positive |
| 1557 | *Salmonella* chicago | *Salmonella* chicago | Positive |
| 1558 | *Salmonella* canastel | *Salmonella* species | Positive |
| 1560 | *Salmonella* westpark | *Salmonella* species | Positive |
| 1566 | *Salmonella* | *Salmonella* | Positive |
| 1568 | *Salmonella* | *Salmonella* arizonae | Positive |
| 1573 | *Salmonella* | *Salmonella* arizonae | Positive |
| 1576 | *Salmonella* | *Salmonella* arizonae | Positive |
| 1585 | *Salmonella* | *Salmonella* arizonae | Positive |
| 1590 | *Salmonella* | *Salmonella* 3b | Positive |
| 1592 | *Salmonella* | *Salmonella* 3b | Positive |
| 1597 | *Salmonella* | *Salmonella* 3b | Positive |
| 1598 | *Salmonella* | *Salmonella* 3b | Positive |
| 1603 | *Salmonella* | *Salmonella* 3b | Positive |
| 1608 | *Salmonella* seminole | *Salmonella* seminole | Positive |
| 1609 | *Salmonella* wassennaar | *Salmonella* wassennaar | Positive |
| 1610 | *Salmonella* seminole | *Salmonella* seminole | Positive |
| 1611 | *Salmonella* | *Salmonella* kralendyk | Positive |
| 1613 | *Salmonella* tuindorp | *Salmonella* kralendyk | Positive |
| 1615 | *Salmonella* chameleon | *Salmonella* kralendyk | Positive |
| 1616 | *Salmonella* houten | *Salmonella* houten | Positive |
| 1620 | *Salmonella* carmel | *Salmonella* carmel | Positive |
| 1621 | *Salmonella* carrau | *Salmonella* carrau | Positive |
| 1623 | *Salmonella* champaign | *Salmonella* champaign | Positive |
| 1624 | *Salmonella* chandans | *Salmonella* chandans | Positive |
| 1625 | *Salmonella* chester | *Salmonella* species | Positive |
| 1628 | *Salmonella* colorado | *Salmonella* species | Positive |
| 1632 | *Salmonella* cubana | *Salmonella* cubana | Positive |
| 1635 | *Salmonella* daytona | *Salmonella* daytona | Positive |
| 1638 | *Salmonella* derby | *Salmonella* derby | Positive |
| 1641 | *Salmonella* durban | *Salmonella* species | Positive |
| 1644 | *Salmonella* ealing | *Salmonella* ealing | Positive |
| 1650 | *Salmonella* livingstone | *Salmonella* livingstone | Positive |
| 1652 | *Salmonella* london | *Salmonella* london | Positive |
| 1653 | *Salmonella* manhattan | *Salmonella* yovokome | Positive |
| 1655 | *Salmonella* reading | *Salmonella* reading | Positive |
| 1657 | *Salmonella* sandiego | *Salmonella* reading | Positive |
| 1658 | *Salmonella* schwarzengrund | *Salmonella* schwarzengrund | Positive |
| 1659 | *Salmonella* shangani | *Salmonella* shangani | Positive |
| 1660 | *Salmonella* sundsvall | *Salmonella* sundsvall | Positive |

TABLE 2-continued

Inclusivity Results

| DuPont Qualicon ID # | Presumptive ID | ID Species | BAX ® System Result |
|---|---|---|---|
| 1661 | *Salmonella* tennessee | *Salmonella* tennessee | Positive |
| 1665 | *Salmonella* colombo | *Salmonella* colombo | Positive |
| 1668 | *Salmonella* california | *Salmonella* california | Positive |
| 1675 | *Salmonella* daressalaam | *Salmonella* enterica | Positive |
| 1680 | *Salmonella* dugbe | *Salmonella* dugbe | Positive |
| 1684 | *Salmonella* emmastad | *Salmonella* emmastad | Positive |
| 1686 | *Salmonella* fayed | *Salmonella* fayed | Positive |
| 1687 | *Salmonella* ferlac | *Salmonella* ferlac | Positive |
| 1689 | *Salmonella* hartford | *Salmonella* species | Positive |
| 1693 | *Salmonella* javiana | *Salmonella* species | Positive |
| 1695 | *Salmonella* johannesburg | *Salmonella* johannesburg | Positive |
| 1698 | *Salmonella* madelia | *Salmonella* madelia | Positive |
| 1700 | *Salmonella* meleagridis | *Salmonella* meleagridis | Positive |
| 1701 | *Salmonella* miami | *Salmonella* miami | Positive |
| 1703 | *Salmonella* mississippi | *Salmonella* mississippi | Positive |
| 1704 | *Salmonella* muenchen | *Salmonella* muenchen | Positive |
| 1707 | *Salmonella* newbrunswick | *Salmonella* newbrunswick | Positive |
| 1710 | *Salmonella* oranienburg | *Salmonella* oranienburg | Positive |
| 1711 | *Salmonella* pomona | *Salmonella* species | Positive |
| 1712 | *Salmonella* pretoria | *Salmonella* pretoria | Positive |
| 1714 | *Salmonella* wassennaar | *Salmonella* wassennaar | Positive |
| 1773 | *Salmonella* enterica | *Salmonella* brookfield | Positive |
| 1775 | *Salmonella* enterica | *Salmonella* typhimurium | Positive |
| 1776 | *Salmonella* enterica | *Salmonella* kralendyk | Positive |
| 1777 | *Salmonella* enterica | *Salmonella* enterica | Positive |
| 2166 | *Salmonella* abaetetuba | *Salmonella* abaetetuba | Positive |
| 2172 | *Salmonella* bareilly | *Salmonella* bareilly | Positive |
| 2178 | *Salmonella* california | *Salmonella* california | Positive |
| 2180 | *Salmonella* champaign | *Salmonella* champaign | Positive |
| 2186 | *Salmonella* drypool | *Salmonella* drypool | Positive |
| 2189 | *Salmonella* give | *Salmonella* give | Positive |
| 2196 | *Salmonella* kiambu | *Salmonella* kiambu | Positive |
| 2199 | *Salmonella* lexington | *Salmonella* lexington | Positive |
| 2201 | *Salmonella* madelia | *Salmonella* madelia | Positive |
| 2204 | *Salmonella* minnesota | *Salmonella* minnesota | Positive |
| 2205 | *Salmonella* mississippi | *Salmonella* mississippi | Positive |
| 2215 | *Salmonella* poona | *Salmonella* poona | Positive |
| 2218 | *Salmonella* sandiego | *Salmonella* sandiego | Positive |
| 2229 | *Salmonella* theilalle | *Salmonella* oranienburg | Positive |
| 2238 | *Salmonella* urbana | *Salmonella* urbana | Positive |
| 2239 | *Salmonella* uzaramo | *Salmonella* cerro | Positive |
| 2245 | *Salmonella* havana | *Salmonella* havana | Positive |
| 2263 | *Salmonella* lille | *Salmonella* lille | Positive |
| 2274 | *Salmonella* anatum | *Salmonella* anatum | Positive |
| 2283 | *Salmonella* newbrunswick | *Salmonella* newbrunswick | Positive |
| 2289 | *Salmonella* rubislaw | *Salmonella* rubislaw | Positive |
| 2290 | *Salmonella* hartford | *Salmonella* hartford | Positive |
| 2309 | *Salmonella* maregrosso | *Salmonella* species | Positive |
| 2312 | *Salmonella* kottbus | *Salmonella* kottbus | Positive |
| 2313 | *Salmonella* wandsworth | *Salmonella* wandsworth | Positive |
| 2341 | *Salmonella* barry | *Salmonella* mbandaka | Positive |
| 2343 | *Salmonella* bockenheim | *Salmonella* kralendyk | Positive |
| 2346 | *Salmonella* vietnam | *Salmonella* vietnam | Positive |
| 2349 | *Salmonella* drypool | *Salmonella* drypool | Positive |
| 2350 | *Salmonella* gallinarum | *Salmonella* gallinarum | Positive |
| 2352 | *Salmonella* saphra | *Salmonella* saphra | Positive |
| 2353 | *Salmonella* kristianstad | *Salmonella* kristianstad | Positive |
| 2373 | *Salmonella* species | *Salmonella* species | Positive |
| 2376 | *Salmonella* species | *Salmonella* sculcoates | Positive |
| 2380 | *Salmonella* species | *Salmonella* sya | Positive |
| 2628 | *Salmonella* kentucky | *Salmonella* kentucky | Positive |
| 2629 | *Salmonella* cerro | *Salmonella* cerro | Positive |
| 2637 | *Salmonella* schwarzengrund | *Salmonella* schwarzengrund | Positive |
| 2639 | *Salmonella* thomasville | *Salmonella* thomasville | Positive |
| 2641 | *Salmonella* schwarzengrund | *Salmonella* schwarzengrund | Positive |
| 2673 | *Salmonella* manhattan | *Salmonella* manhattan | Positive |
| 2736 | *Salmonella* oranienburg | *Salmonella* oranienburg | Positive |
| 2748 | *Salmonella* muenster | *Salmonella* muenster | Positive |
| 2755 | *Salmonella* mbandaka | *Salmonella* mbandaka | Positive |
| 2757 | *Salmonella* mbandaka | *Salmonella* mbandaka | Positive |
| 2761 | *Salmonella* mbandaka | *Salmonella* mbandaka | Positive |
| 2766 | *Salmonella* mbandaka | *Salmonella* mbandaka | Positive |
| 2770 | *Salmonella* mbandaka | *Salmonella* mbandaka | Positive |
| 2774 | *Salmonella* mbandaka | *Salmonella* mbandaka | Positive |

TABLE 2-continued

Inclusivity Results

| DuPont Qualicon ID # | Presumptive ID | ID Species | BAX ® System Result |
|---|---|---|---|
| 2779 | *Salmonella* mbandaka | *Salmonella* mbandaka | Positive |
| 2786 | *Salmonella* binza | *Salmonella* binza | Positive |
| 2795 | *Salmonella* berta | *Salmonella* berta | Positive |
| 2813 | *Salmonella* cerro | *Salmonella* cerro | Positive |
| 2820 | *Salmonella* braenderup | *Salmonella* braenderup | Positive |
| 2867 | *Salmonella* sya | *Salmonella* sya | Positive |
| 2868 | *Salmonella* lille | *Salmonella* lille | Positive |
| 2869 | *Salmonella* durham | *Salmonella* durham | Positive |
| 2870 | *Salmonella* corvallis | *Salmonella* bellevue | Positive |
| 2935 | *Salmonella* sandiego | *Salmonella* sandiego | Positive |
| 2966 | *Salmonella* albany | *Salmonella* albany | Positive |
| 2980 | *Salmonella* arkansas | *Salmonella* arkansas | Positive |
| 2981 | *Salmonella* arkansas | *Salmonella* arkansas | Positive |
| 2992 | *Salmonella* lille | *Salmonella* lille | Positive |
| 3015 | *Salmonella* dublin | *Salmonella* dublin | Positive |
| 3017 | *Salmonella* dublin | *Salmonella* dublin | Positive |
| 3019 | *Salmonella* dublin | *Salmonella* dublin | Positive |
| 3038 | *Salmonella* krefeld | *Salmonella* krefeld | Positive |
| 3043 | *Salmonella* johannesburg | *Salmonella* johannesburg | Positive |
| 3153 | *Salmonella* chandans | *Salmonella* chandans | Positive |
| 3156 | *Salmonella* muenchen | *Salmonella* muenchen | Positive |
| 3157 | *Salmonella* corvallis | *Salmonella* bellevue | Positive |
| 3184 | *Salmonella* sculcoates | *Salmonella* sculcoates | Positive |
| 3185 | *Salmonella* bellevue | *Salmonella* bellevue | Positive |
| 3186 | *Salmonella* sya | *Salmonella* sya | Positive |
| 3187 | *Salmonella* durham | *Salmonella* durham | Positive |
| 3194 | *Salmonella* stanleyville | *Salmonella* stanleyville | Positive |
| 3217 | *Salmonella* cotham | *Salmonella* cotham | Positive |
| 3218 | *Salmonella* agama | *Salmonella* agama | Positive |
| 3432 | *Salmonella* amager | *Salmonella* amager | Positive |
| 3510 | *Salmonella* oslo | unknown | Positive |
| 3536 | *Salmonella* tennessee | *Salmonella* tennessee | Positive |
| 3699 | *Salmonella* hvittingfoss | *Salmonella* species | Positive |
| 3852 | *Salmonella* indiana | *Salmonella* indiana | Positive |
| 3863 | *Salmonella* othmarschen | *Salmonella* oranienburg | Positive |
| 3878 | *Salmonella* mbandaka | *Salmonella* mbandaka | Positive |
| 3882 | *Salmonella* broughton | *Salmonella* minnesota | Positive |
| 3898 | *Salmonella* neumuenster | *Salmonella* thompson | Positive |
| 3915 | *Salmonella* haardt | *Salmonella* haardt | Positive |
| 3917 | *Salmonella* hadar | *Salmonella* hadar | Positive |
| 3918 | *Salmonella* hadar | *Salmonella* hadar | Positive |
| 3924 | *Salmonella* thomasville | *Salmonella* thomasville | Positive |
| 3984 | *Salmonella* choleraesuis | *Salmonella* java | Positive |
| 3988 | *Salmonella* choleraesuis | *Salmonella* choleraesuis | Positive |
| 4011 | *Salmonella* mbandaka | *Salmonella* mbandaka | Positive |
| 4022 | *Salmonella* enteritidis | *Salmonella* enteritidis | Positive |
| 4035 | *Salmonella* waycross | *Salmonella* waycross | Positive |
| 4036 | *Salmonella* livingstone | *Salmonella* livingstone | Positive |
| 4043 | *Salmonella* worthington | *Salmonella* worthington | Positive |
| 4084 | *Salmonella* africana | *Salmonella* thompson | Positive |
| 4102 | *Salmonella* species | *Salmonella* saintpaul | Positive |
| 4558 | *Salmonella* redlands | *Salmonella* redlands | Positive |
| 5533 | *Salmonella* infantis | *Salmonella* infantis | Positive |
| 5908 | *Salmonella* ferlac | *Salmonella* ferlac | Positive |
| 6177 | *Salmonella* species | *Salmonella* arkansas | Positive |
| 6250 | *Salmonella* santiago | *Salmonella* santiago | Positive |
| 6586 | *Salmonella* santiago | *Salmonella* santiago | Positive |
| 6667 | *Salmonella* heidelberg | *Salmonella* heidelberg | Positive |
| 6696 | *Salmonella* species | *Salmonella* enteritidis | Positive |
| 6729 | *Salmonella* manila | *Salmonella* manila | Positive |
| 6735 | *Salmonella* species | *Salmonella* albany | Positive |
| 6966 | *Salmonella* cotham | *Salmonella* cotham | Positive |
| 7005 | *Salmonella* dublin | *Salmonella* species | Positive |
| 7061 | *Salmonella* kubacha | *Salmonella* kubacha | Positive |
| 7062 | *Salmonella* kubacha | *Salmonella* kubacha | Positive |
| 7072 | *Salmonella* amsterdam | *Salmonella* amsterdam | Positive |
| 7111 | *Salmonella* infantis | *Salmonella* infantis | Positive |
| 8034 | *Salmonella* species | *Salmonella* saintpaul | Positive |
| 12241 | *Salmonella* species | *Salmonella* species | Positive |
| 12904 | *Salmonella* tranorora | *Salmonella* enterica | Positive |
| 12907 | *Salmonella* heidelberg | *Salmonella* heidelberg | Positive |
| 12908 | *Salmonella* heidelberg | *Salmonella* heidelberg | Positive |
| 12909 | *Salmonella* heidelberg | *Salmonella* heidelberg | Positive |
| 12910 | *Salmonella* heidelberg | *Salmonella* heidelberg | Positive |

TABLE 2-continued

Inclusivity Results

| DuPont Qualicon ID # | Presumptive ID | ID Species | BAX ® System Result |
|---|---|---|---|
| 12911 | *Salmonella* heidelberg | *Salmonella* heidelberg | Positive |
| 12912 | *Salmonella* kentucky | *Salmonella* kentucky | Positive |
| 12913 | *Salmonella* heidelberg | *Salmonella* heidelberg | Positive |
| 12914 | *Salmonella* kentucky | *Salmonella* kentucky | Positive |
| 12915 | *Salmonella* kentucky | *Salmonella* kentucky | Positive |
| 12916 | *Salmonella* kentucky | *Salmonella* kentucky | Positive |
| 12917 | *Salmonella* kentucky | *Salmonella* kentucky | Positive |
| 12918 | *Salmonella* kentucky | *Salmonella* kentucky | Positive |
| 12919 | *Salmonella* heidelberg | *Salmonella* heidelberg | Positive |
| 12920 | *Salmonella* heidelberg | *Salmonella* heidelberg | Positive |
| 12921 | *Salmonella* kentucky | *Salmonella* kentucky | Positive |
| 12922 | *Salmonella* heidelberg | *Salmonella* heidelberg | Positive |
| 12925 | *Salmonella* kentucky | *Salmonella* kentucky | Positive |
| 12926 | *Salmonella* kentucky | *Salmonella* kentucky | Positive |
| 12927 | *Salmonella* kentucky | *Salmonella* kentucky | Positive |
| 12928 | *Salmonella* heidelberg | *Salmonella* heidelberg | Positive |
| 12929 | *Salmonella* heidelberg | *Salmonella* heidelberg | Positive |
| 12931 | *Salmonella* heidelberg | *Salmonella* heidelberg | Positive |
| 12932 | *Salmonella* heidelberg | *Salmonella* heidelberg | Positive |
| 12933 | *Salmonella* heidelberg | *Salmonella* heidelberg | Positive |
| 12936 | *Salmonella* heidelberg | *Salmonella* heidelberg | Positive |
| 12937 | *Salmonella* heidelberg | *Salmonella* heidelberg | Positive |
| 12941 | *Salmonella* kentucky | *Salmonella* kentucky | Positive |
| 12943 | *Salmonella* kentucky | *Salmonella* kentucky | Positive |
| 12945 | *Salmonella* heidelberg | *Salmonella* heidelberg | Positive |
| 12946 | *Salmonella* kentucky | *Salmonella* kentucky | Positive |
| 12947 | *Salmonella* heidelberg | *Salmonella* heidelberg | Positive |
| 12948 | *Salmonella* kentucky | *Salmonella* kentucky | Positive |
| 12949 | *Salmonella* kentucky | *Salmonella* kentucky | Positive |
| 12950 | *Salmonella* kentucky | *Salmonella* kentucky | Positive |
| 12951 | *Salmonella* kentucky | *Salmonella* kentucky | Positive |
| 12952 | *Salmonella* heidelberg | *Salmonella* heidelberg | Positive |
| 12953 | *Salmonella* heidelberg | *Salmonella* heidelberg | Positive |
| 12954 | *Salmonella* heidelberg | *Salmonella* heidelberg | Positive |
| 12955 | *Salmonella* kentucky | *Salmonella* kentucky | Positive |
| 12956 | *Salmonella* kentucky | *Salmonella* kentucky | Positive |
| 12957 | *Salmonella* kentucky | *Salmonella* kentucky | Positive |
| 12959 | *Salmonella* heidelberg | *Salmonella* heidelberg | Positive |
| 12960 | *Salmonella* senftenberg | *Salmonella* senftenberg | Positive |
| 12961 | *Salmonella* senftenberg | *Salmonella* senftenberg | Positive |
| 12962 | *Salmonella* senftenberg | *Salmonella* senftenberg | Positive |
| 12963 | *Salmonella* senftenberg | *Salmonella* senftenberg | Positive |
| 12964 | *Salmonella* senftenberg | *Salmonella* senftenberg | Positive |
| 12965 | *Salmonella* senftenberg | *Salmonella* senftenberg | Positive |
| 12966 | *Salmonella* senftenberg | *Salmonella* senftenberg | Positive |
| 12967 | *Salmonella* haardt | *Salmonella* haardt | Positive |
| 12968 | *Salmonella* haardt | *Salmonella* haardt | Positive |
| 12969 | *Salmonella* haardt | *Salmonella* haardt | Positive |
| 12970 | *Salmonella* senftenberg | *Salmonella* senftenberg | Positive |
| 12971 | *Salmonella* senftenberg | *Salmonella* senftenberg | Positive |
| 12972 | *Salmonella* senftenberg | *Salmonella* senftenberg | Positive |
| 12975 | *Salmonella* senftenberg | *Salmonella* senftenberg | Positive |
| 12978 | *Salmonella* senftenberg | *Salmonella* senftenberg | Positive |
| 12980 | *Salmonella* senftenberg | *Salmonella* senftenberg | Positive |
| 12981 | *Salmonella* kentucky | *Salmonella* kentucky | Positive |
| 12982 | *Salmonella* senftenberg | *Salmonella* senftenberg | Positive |
| 12983 | *Salmonella* senftenberg | *Salmonella* senftenberg | Positive |
| 12984 | *Salmonella* senftenberg | *Salmonella* senftenberg | Positive |
| 12985 | *Salmonella* haardt | *Salmonella* haardt | Positive |
| 12986 | *Salmonella* senftenberg | *Salmonella* senftenberg | Positive |
| 12987 | *Salmonella* senftenberg | *Salmonella* senftenberg | Positive |
| 12988 | *Salmonella* senftenberg | *Salmonella* senftenberg | Positive |
| 12989 | *Salmonella* kentucky | *Salmonella* kentucky | Positive |
| 12990 | *Salmonella* kentucky | *Salmonella* kentucky | Positive |
| 12993 | *Salmonella* kentucky | *Salmonella* kentucky | Positive |
| 12995 | *Salmonella* heidelberg | *Salmonella* heidelberg | Positive |
| 12996 | *Salmonella* heidelberg | *Salmonella* heidelberg | Positive |
| 12997 | *Salmonella* kentucky | *Salmonella* kentucky | Positive |
| 12998 | *Salmonella* heidelberg | *Salmonella* heidelberg | Positive |
| 12999 | *Salmonella* heidelberg | *Salmonella* heidelberg | Positive |
| 13000 | *Salmonella* heidelberg | *Salmonella* heidelberg | Positive |
| 13001 | *Salmonella* heidelberg | *Salmonella* heidelberg | Positive |
| 13002 | *Salmonella* kentucky | *Salmonella* kentucky | Positive |
| 13003 | *Salmonella* kentucky | *Salmonella* kentucky | Positive |

TABLE 2-continued

Inclusivity Results

| DuPont Qualicon ID # | Presumptive ID | ID Species | BAX ® System Result |
|---|---|---|---|
| 13004 | *Salmonella* heidelberg | *Salmonella* heidelberg | Positive |
| 13005 | *Salmonella* typhimurium | *Salmonella* typhimurium | Positive |
| 13006 | *Salmonella* kentucky | *Salmonella* kentucky | Positive |
| 13007 | *Salmonella* kentucky | *Salmonella* kentucky | Positive |
| 13008 | *Salmonella* kentucky | *Salmonella* kentucky | Positive |
| 13009 | *Salmonella* kentucky | *Salmonella* kentucky | Positive |
| 13010 | *Salmonella* kentucky | *Salmonella* kentucky | Positive |
| 13011 | *Salmonella* typhimurium | *Salmonella* typhimurium | Positive |
| 13012 | *Salmonella* kentucky | *Salmonella* kentucky | Positive |
| 13013 | *Salmonella* kentucky | *Salmonella* kentucky | Positive |
| 13014 | *Salmonella* heidelberg | *Salmonella* heidelberg | Positive |
| 13015 | *Salmonella* kentucky | *Salmonella* kentucky | Positive |
| 13016 | *Salmonella* kentucky | *Salmonella* kentucky | Positive |
| 13017 | *Salmonella* heidelberg | *Salmonella* heidelberg | Positive |
| 13018 | *Salmonella* heidelberg | *Salmonella* heidelberg | Positive |
| 13019 | *Salmonella* heidelberg | *Salmonella* heidelberg | Positive |
| 13020 | *Salmonella* heidelberg | *Salmonella* heidelberg | Positive |
| 13021 | *Salmonella* heidelberg | *Salmonella* heidelberg | Positive |
| 13022 | *Salmonella* heidelberg | *Salmonella* heidelberg | Positive |
| 13035 | *Salmonella* enterica | *Salmonella* enterica | Positive |
| 13036 | *Salmonella* enterica | *Salmonella* enterica | Positive |
| 13037 | *Salmonella* species | *Salmonella* species | Positive |
| 13056 | *Salmonella* senftenberg | *Salmonella* senftenberg | Positive |
| 13057 | *Salmonella* senftenberg | *Salmonella* senftenberg | Positive |
| 13058 | *Salmonella* senftenberg | *Salmonella* senftenberg | Positive |
| 13059 | *Salmonella* senftenberg | *Salmonella* senftenberg | Positive |
| 13060 | *Salmonella* senftenberg | *Salmonella* senftenberg | Positive |
| 13061 | *Salmonella* tennessee | *Salmonella* tennessee | Positive |
| 13062 | *Salmonella* tennessee | *Salmonella* tennessee | Positive |
| 13063 | *Salmonella* tennessee | *Salmonella* tennessee | Positive |
| 13064 | *Salmonella* tennessee | *Salmonella* tennessee | Positive |
| 13065 | *Salmonella* tennessee | *Salmonella* tennessee | Positive |
| 13066 | *Salmonella* tennessee | *Salmonella* tennessee | Positive |
| 13067 | *Salmonella* havana | *Salmonella* havana | Positive |
| 13068 | *Salmonella* lexington | *Salmonella* lexington | Positive |
| 13069 | *Salmonella* mbandaka | *Salmonella* mbandaka | Positive |
| 13070 | *Salmonella* species | *Salmonella* species | Positive |
| 13075 | *Salmonella* species | *Salmonella* cubana | Positive |
| 13079 | *Salmonella* newport | *Salmonella* newport | Positive |
| 13080 | *Salmonella* saintpaul | *Salmonella* saintpaul | Positive |
| 13081 | *Salmonella* virchow | *Salmonella* virchow | Positive |
| S-1 | *Salmonella* | Newport | Positive |
| S-4 | *Salmonella* | *Typhimurium* | Positive |
| S-45 | *Salmonella* | V48:i:- | Positive |
| S-46 | *Salmonella* | V 40:z35:- | Positive |
| S-47 | *Salmonella* | V 44:z39:- | Positive |
| S-48 | *Salmonella* | V 60:z41:- | Positive |
| S-49 | *Salmonella* | V 66:z41> | Positive |
| S-5 | *Salmonella* | *Typhi* | Positive |
| S-50 | *Salmonella* | V48:z35:- | Positive |
| S-51 | *Salmonella* | VI 6,14,25:zI0:I,(2),7 | Positive |
| S-52 | *Salmonella* | VI II:b:I,7 | Positive |
| S-53 | *Salmonella* | VI 6,7:z41:I,7 | Positive |
| S-54 | *Salmonella* | VI II:a:I,5 | Positive |
| S-55 | *Salmonella* | VI 6,14,25:a:e,n,x | Positive |
| S-56 | *Salmonella* | *Typhimurium*/DTI 04b | Positive |
| S-57 | *Salmonella* | *Typhimurium* | Positive |
| S-58 | *Salmonella* | *Typhimurium* | Positive |
| S-59 | *Salmonella* | *Typhimurium* | Positive |
| S-60 | *Salmonella* | *Typhimurium* | Positive |
| S-61 | *Salmonella* | *Typhimurium* | Positive |
| S-62 | *Salmonella* | *Typhimurium* | Positive |
| S-63 | *Salmonella* | *Typhimurium* | Positive |
| S-64 | *Salmonella* | *Typhimurium* | Positive |
| S-65 | *Salmonella* | *Typhimurium* | Positive |
| S-66 | *Salmonella* | *Typhimurium* | Positive |
| S-67 | *Salmonella* | *Typhimurium* | Positive |
| S-68 | *Salmonella* | *Typhimurium* | Positive |
| S-69 | *Salmonella* | *Typhimurium* | Positive |
| S-70 | *Salmonella* | *Typhimurium*/DTI 04 | Positive |
| S-71 | *Salmonella* | *Typhimurium*/DTI 04 | Positive |
| S-72 | *Salmonella* | *Typhimurium*/DTI 04 | Positive |
| S-8 | *Salmonella* | Virchow | Positive |
| S-82 | *Salmonella* | Saphra | Positive |

TABLE 2-continued

Inclusivity Results

| DuPont Qualicon ID # | Presumptive ID | ID Species | BAX ® System Result |
|---|---|---|---|
| S-83 | *Salmonella* | Rubislaw | Positive |
| S-84 | *Salmonella* | Michigan | Positive |
| S-85 | *Salmonella* | Urbana | Positive |
| S-86 | *Salmonella* | Vietnam | Positive |
| S-87 | *Salmonella* | Tornow | Positive |
| S-92 | *Salmonella* | Muenchen | Positive |
| S-93 | *Salmonella* | Senftenberg | Positive |
| S-94 | *Salmonella* | Muenster | Positive |
| S-95 | *Salmonella* | Montevideo | Positive |

TABLE 3

Exclusivity Results

| DuPont Qualicon ID# | ID Species | BAX ® System Result |
|---|---|---|
| DD2901 | *Bacillus cereus* | Negative |
| DD2558 | *Citrobacter freundii* | Negative |
| DD383 | *Citrobacter freundii* | Negative |
| DD1725 | *E. coli* O125:H19 | Negative |
| DD2614 | *Edwardsiella tarda* | Negative |
| DD11348 | *Enterobacter sakazakii* | Negative |
| DD3981 | *Enterococcus faecalis* | Negative |
| DD846 | *Escherichia blattae* | Negative |
| DD641 | *Escherichia coli* | Negative |
| DD640 | *Escherichia coli* O157:H7 | Negative |
| DD847 | *Escherichia* ferguson | Negative |
| DD6719 | *Escherichia hermanii* | Negative |
| DD849 | *Escherichia intermedia* | Negative |
| DD850 | *Escherichia vulnaris* | Negative |
| DD6121 | Gram negative rod | Negative |
| DD2389 | *Hafnia alvei* | Negative |
| DD5588 | *Hafnia alvei* | Negative |
| DD6523 | *Klebsiella oxytoca* | Negative |
| DD658 | *Klebsiella oxytoca* | Negative |
| DD657 | *Klebsiella ozaenae* | Negative |
| DD373 | *Klebsiella pneumoniae* | Negative |
| DD7344 | *Lactobacillus acidophilus* | Negative |
| DD687 | *Lactobacillus carnis* | Negative |
| DD922 | *Listeria innocua* | Negative |
| DD1152 | *Listeria monocytogenes* | Negative |
| DD13142 | *Morganella morganii* | Negative |
| DD3064 | *Morganella morganii* | Negative |
| DD374 | *Proteus mirabilis* | Negative |
| DD13147 | *Providencia rettgeri* | Negative |
| DD13148 | *Pseudomonas aeruginosa* | Negative |
| DD3982 | *Pseudomonas aeruginosa* | Negative |
| DD569 | *Pseudomonas fluorescens* | Negative |
| DD661 | *Pseudomonas fluorescens* | Negative |
| DD577 | *Pseudomonas stutzeri* | Negative |
| DD2166 | *Salmonella abaetetuba* | Negative |
| DD3017 | *Salmonella* dublin | Negative |
| DD3019 | *Salmonella* dublin | Negative |
| DD1777 | *Salmonella enterica* | Negative |
| DD2416 | *Serratia liquefaciens* | Negative |
| DD2417 | *Serratia liquefaciens* | Negative |
| DD1081 | *Shigella boydii* | Negative |
| DD6832 | *Shigella sonnei* | Negative |
| DD4160 | *Staphylococcus aureus* | Negative |
| DD610 | *Staphylococcus aureus* | Negative |
| DD3998 | *Streptococcus equi* | Negative |
| DD7083 | Unknown | Negative |
| TD3136 | *Vibrio cholera* | Negative |
| DD13249 | *Vibrio parahemolyticus* | Negative |
| TD3122 | *Vibrio vulnificus* | Negative |

What is claimed is:

1. A method for detecting the presence of *Salmonella* in a sample, said sample comprising nucleic acids, said method comprising
    (a) providing a reaction mixture comprising at least one primer and probe, wherein said primer is at least 11 nucleotides in length and said probe is at least 14 nucleotides in length, and wherein
        (i) said primer comprises a nucleic acid sequence capable of selectively hybridizing at a Tm higher than 55° C. to the sequence of SEQ ID NO: 1 or a sequence fully complementary thereto, and said probe comprises a nucleic acid sequence capable of selectively hybridizing at a Tm higher than 55° C. to the sequence of SEQ ID NO: 2 or a sequence fully complementary thereto; or
        (ii) said primer comprises a nucleic acid sequence capable of selectively hybridizing at a Tm higher than 55° C. to the nucleic acid sequence of SEQ ID NO: 3 or a sequence fully complementary thereto, and said probe comprises a nucleic acid sequence capable of selectively hybridizing at a Tm higher than 55° C. to the sequence of SEQ ID NO: 4 or a sequence fully complementary thereto; and
    (b) performing PCR amplification of said nucleic acids of said sample using the reaction mixture of step (a); and
    (c) detecting the amplification of step (b), whereby a positive detection of said amplification indicates the presence of *Salmonella* in said sample.

2. The method of claim 1, wherein said reaction mixture comprises both the primer and probe of (i) and the primer and probe of (ii).

3. The method of claim 1, wherein said primer and probe each possess a 3' terminus and a 5' terminus, and wherein the 3' terminus of said probe is directly or indirectly attached to the 5' terminus of the primer, thereby forming a primer-probe complex.

4. The method of claim 3, wherein said primer-probe complex comprises a detectable label.

5. The method of claim 1, wherein said primer capable of selectively hybridizing to SEQ ID NO: 1 comprises a nucleic acid sequence selected from the group consisting of SEQ ID NOS: 40-54, and wherein said probe capable of selectively hybridizing to SEQ ID NO: 2 comprises a nucleic acid sequence selected from the group consisting of SEQ ID NOS: 6-39.

6. The method of claim 3, wherein said primer-probe complex further comprises a 5' Stem Sequence and a 3' Stem Sequence, wherein the 3' terminus of the 5' Stem Sequence is directly or indirectly attached to the 5' terminus of the probe, wherein the 5' terminus of the 3' Stem Sequence is directly or indirectly attached to the 3' terminus of the probe, and wherein the 3' terminus of the 3' Stem Sequence is directly or indirectly attached of the 5' terminus of the primer.

7. The method of claim 6, wherein said 5' Stem Sequence comprises a nucleic acid sequence selected from the group consisting of SEQ ID NOS: 112-119, and wherein said 3' Stem Sequence comprises a nucleic acid sequence selected from the group consisting of SEQ ID NOS: 120-130.

8. The method of claim 1, wherein said reaction mixture further comprises a quencher oligonucleotide capable of selectively hybridizing at a Tm higher than 55° C. to the probe.

* * * * *